US012544110B2

(12) United States Patent
McBride et al.

(10) Patent No.: US 12,544,110 B2
(45) Date of Patent: Feb. 10, 2026

(54) SPINAL IMPLANT SYSTEM AND METHOD

(71) Applicant: Warsaw Orthopedic, Inc., Warsaw, IN (US)

(72) Inventors: Larry T. McBride, Germantown, TN (US); Rex W. Armstrong, Cordova, TN (US); Domagoj Coric, Charlotte, NC (US); Robert M. Loke, Memphis, TN (US)

(73) Assignee: WARSAW ORTHOPEDIC, INC., Warsaw, IN (US)

(*) Notice: Subject to any disclaimer, the term of this patent is extended or adjusted under 35 U.S.C. 154(b) by 141 days.

(21) Appl. No.: 18/403,112

(22) Filed: Jan. 3, 2024

(65) Prior Publication Data

US 2024/0138881 A1 May 2, 2024

Related U.S. Application Data

(63) Continuation of application No. 17/976,163, filed on Oct. 28, 2022, now Pat. No. 11,890,033.

(51) Int. Cl.
*A61B 17/88* (2006.01)
*A61B 17/70* (2006.01)

(52) U.S. Cl.
CPC ...... *A61B 17/7032* (2013.01); *A61B 17/7035* (2013.01)

(58) Field of Classification Search
CPC ........................ A61B 17/7032; A61B 17/7035
USPC ................................ 606/265–267, 270, 279
See application file for complete search history.

(56) References Cited

U.S. PATENT DOCUMENTS

| | | | |
|---|---|---|---|
| 5,207,678 | A | 5/1993 | Harms et al. |
| 5,443,467 | A | 8/1995 | Biedermann et al. |
| 5,575,792 | A | 11/1996 | Errico et al. |
| 5,609,593 | A | 3/1997 | Errico et al. |
| 5,609,654 | A | 3/1997 | Le et al. |
| 5,630,817 | A | 5/1997 | Rokegem et al. |
| 5,643,263 | A | 7/1997 | Simonson |
| 5,797,911 | A | 8/1998 | Sherman et al. |

(Continued)

FOREIGN PATENT DOCUMENTS

| | | |
|---|---|---|
| CN | 101594832 | 12/2009 |
| CN | 102596067 | 7/2012 |

(Continued)

OTHER PUBLICATIONS

International Search Report and Written Opinion for International (PCT) Patent Application No. PCT/IB2023/062256, dated Mar. 20, 2024, 16 pages.

(Continued)

*Primary Examiner* — Eduardo C Robert
*Assistant Examiner* — David C Comstock
(74) *Attorney, Agent, or Firm* — Sheridan Ross P.C.

(57) ABSTRACT

A spinal implant includes a receiver having a first arm connected to a first extension and a second arm connected to a second extension. The arms are connected to the extensions via a break away surface. The arms include a proximal most end surface and the receiver includes an implant receiving surface. The proximal most end surface and the implant receiving surface defining an implant cavity. The break away surface is disposed within the implant cavity. In some embodiments, systems, spinal constructs and methods are disclosed.

19 Claims, 30 Drawing Sheets

(56) References Cited

U.S. PATENT DOCUMENTS

| | | | | |
|---|---|---|---|---|
| 5,885,285 | A | 3/1999 | Simonson | |
| 5,885,286 | A | 3/1999 | Sherman et al. | |
| 5,947,967 | A | 9/1999 | Barker | |
| 6,074,391 | A | 6/2000 | Metz-Stavenhagen et al. | |
| 6,226,548 | B1 | 5/2001 | Foley et al. | |
| 6,280,442 | B1 | 8/2001 | Barker et al. | |
| 6,520,962 | B1 | 2/2003 | Taylor et al. | |
| 6,562,038 | B1 | 5/2003 | Morrison | |
| 6,572,618 | B1 | 6/2003 | Morrison | |
| 6,579,292 | B2 | 6/2003 | Taylor | |
| 6,648,887 | B2 | 11/2003 | Ashman | |
| 6,685,705 | B1 | 2/2004 | Taylor | |
| 6,755,830 | B2 | 6/2004 | Minfelde et al. | |
| 6,872,209 | B2 | 3/2005 | Morrison | |
| 7,066,939 | B2 | 6/2006 | Taylor | |
| 7,867,255 | B2 | 1/2011 | Miller et al. | |
| 7,927,360 | B2 * | 4/2011 | Pond, Jr. | A61B 17/7037 606/267 |
| 7,976,567 | B2 | 7/2011 | Null et al. | |
| 8,277,489 | B2 | 10/2012 | Saidha et al. | |
| 8,298,275 | B2 | 10/2012 | Rezach | |
| 8,419,773 | B2 | 4/2013 | Biedermann et al. | |
| 8,430,913 | B2 | 4/2013 | James et al. | |
| 8,523,911 | B2 | 9/2013 | Jani et al. | |
| 8,535,352 | B2 | 9/2013 | Altarac et al. | |
| 8,585,741 | B2 | 11/2013 | Gabelberger et al. | |
| 8,672,978 | B2 | 3/2014 | Dant et al. | |
| 8,795,337 | B2 | 8/2014 | Wilcox et al. | |
| 8,992,575 | B1 | 3/2015 | Di Lauro et al. | |
| 9,155,580 | B2 | 10/2015 | Cormier et al. | |
| 9,247,964 | B1 | 2/2016 | Shoshtaev | |
| 9,314,274 | B2 | 4/2016 | Amstutz et al. | |
| 9,387,013 | B1 | 7/2016 | Shoshtaev et al. | |
| 9,402,663 | B2 | 8/2016 | Peterson et al. | |
| 9,629,663 | B2 | 4/2017 | Ludwig et al. | |
| 10,238,432 | B2 | 3/2019 | Carruth et al. | |
| 10,335,201 | B2 * | 7/2019 | Rezach | A61B 17/7032 |
| 10,413,331 | B2 | 9/2019 | Gregory | |
| 10,736,665 | B2 | 8/2020 | Bobbitt et al. | |
| 10,835,291 | B2 | 11/2020 | May | |
| 10,966,760 | B2 | 4/2021 | Armstrong et al. | |
| 11,147,593 | B2 | 10/2021 | Biedermann et al. | |
| 11,234,738 | B2 | 2/2022 | Jackson et al. | |
| 11,291,477 | B1 | 4/2022 | Rezach et al. | |
| 11,890,033 | B1 | 2/2024 | McBride et al. | |
| 2002/0029040 | A1 | 3/2002 | Morrison et al. | |
| 2004/0162558 | A1 | 8/2004 | Hegde et al. | |
| 2005/0049588 | A1 | 3/2005 | Jackson | |
| 2005/0197660 | A1 * | 9/2005 | Haid, Jr. | A61B 17/7064 606/279 |
| 2005/0228326 | A1 | 10/2005 | Kalfas et al. | |
| 2005/0240180 | A1 | 10/2005 | Vienney et al. | |
| 2005/0273101 | A1 | 12/2005 | Schumacher | |
| 2006/0058794 | A1 | 3/2006 | Jackson | |
| 2006/0083603 | A1 | 4/2006 | Jackson | |
| 2007/0055244 | A1 | 3/2007 | Jackson | |
| 2007/0191840 | A1 | 8/2007 | Pond, Jr. et al. | |
| 2008/0015584 | A1 | 1/2008 | Richelsoph | |
| 2008/0177323 | A1 | 7/2008 | Null et al. | |
| 2008/0183215 | A1 | 7/2008 | Altarac et al. | |
| 2008/0262553 | A1 | 10/2008 | Hawkins et al. | |
| 2008/0294194 | A1 | 11/2008 | Capote et al. | |
| 2010/0087864 | A1 | 4/2010 | Klein et al. | |
| 2010/0087867 | A1 | 4/2010 | Klein et al. | |
| 2010/0094345 | A1 | 4/2010 | Saidha et al. | |
| 2010/0160981 | A1 | 6/2010 | Butler et al. | |
| 2010/0318131 | A1 | 12/2010 | James et al. | |
| 2010/0324599 | A1 | 12/2010 | Montello et al. | |
| 2011/0257690 | A1 | 10/2011 | Rezach | |
| 2012/0046701 | A1 | 2/2012 | Gennari et al. | |
| 2012/0109208 | A1 | 5/2012 | Justis et al. | |
| 2012/0130436 | A1 | 5/2012 | Haskins et al. | |
| 2014/0214084 | A1 | 7/2014 | Jackson et al. | |
| 2015/0351809 | A1 | 12/2015 | Jackson et al. | |
| 2016/0166289 | A1 | 6/2016 | Alsup et al. | |
| 2017/0348026 | A1 | 12/2017 | Stein et al. | |
| 2018/0206890 | A1 | 7/2018 | Rezach | |
| 2018/0228516 | A1 | 8/2018 | Armstrong et al. | |
| 2018/0228518 | A1 | 8/2018 | Carruth et al. | |
| 2018/0243009 | A1 | 8/2018 | Bobbitt et al. | |
| 2019/0029729 | A1 | 1/2019 | Mire et al. | |
| 2019/0150990 | A1 * | 5/2019 | Jackson | A61B 17/7037 |
| 2020/0146724 | A1 | 5/2020 | Italiaie | |
| 2020/0268452 | A1 * | 8/2020 | Rezach | A61B 34/30 |
| 2020/0405395 | A1 * | 12/2020 | Gullotti | A61B 17/809 |
| 2021/0145519 | A1 * | 5/2021 | Mosnier | A61B 34/20 |
| 2021/0153904 | A1 | 5/2021 | Armstrong et al. | |
| 2021/0169531 | A1 | 6/2021 | Leff et al. | |
| 2021/0220018 | A1 | 7/2021 | Armstrong et al. | |
| 2024/0188992 | A1 | 6/2024 | Dewey et al. | |

FOREIGN PATENT DOCUMENTS

| | | | |
|---|---|---|---|
| CN | 202932996 | 3/2013 | |
| CN | 103025255 | 4/2013 | |
| CN | 103153219 | 6/2013 | |
| DE | 202011107821 | 2/2012 | |
| DE | 102011111403 | 10/2012 | |
| EP | 3579770 | 12/2019 | |
| FR | 2859620 | 3/2005 | |
| WO | WO 2014/138614 | 9/2014 | |
| WO | WO2015184012 A3 * | 12/2015 | A61B 17/7002 |

OTHER PUBLICATIONS

International Search Report and Written Opinion for International (PCT) Patent Application No. PCT/IB2023/060616, dated Jan. 29, 2024, 13 pages.

Official Action for China Patent Application No. 201810132125.8, dated Jan. 10, 2022, 22 pages.

Article 94(3) Communication for Europe Patent Application No. 18152721.9, dated Jun. 18, 2021, 7 pages.

Article 94(3) Communication for Europe Patent Application No. 18152721.9, dated Mar. 15, 2023, 4 pages.

Official Action for U.S. Appl. No. 17/976,163, dated Jun. 26, 2023, 12 pages.

Notice of Allowance for U.S. Appl. No. 17/976,163, dated Oct. 2, 2023, 5 pages.

Official Action for U.S. Appl. No. 15/337,229, dated May 11, 2017, 12 pages.

Official Action for U.S. Appl. No. 15/337,229, dated Dec. 14, 2017, 12 pages.

Official Action for U.S. Appl. No. 15/337,229, dated Apr. 3, 2018, 13 pages.

Official Action for U.S. Appl. No. 15/337,229, dated Oct. 19, 2018, 18 pages.

Official Action for U.S. Appl. No. 15/337,229, dated Apr. 3, 2019, 19 pages.

Official Action for U.S. Appl. No. 15/337,229, dated Oct. 11, 2019, 7 pages.

Official Action for U.S. Appl. No. 15/337,229, dated Feb. 7, 2020, 21 pages.

Notice of Allowance for U.S. Appl. No. 15/337,229, dated Dec. 11, 2020, 5 pages.

Official Action for U.S. Appl. No. 15/432,704, dated Aug. 1, 2018, 6 pages. Restriction Requirement.

Official Action for U.S. Appl. No. 15/432,704, dated Oct. 15, 2024, 10 pages.

Official Action for U.S. Appl. No. 15/432,704, dated Apr. 22, 2019, 23 pages.

Official Action for U.S. Appl. No. 15/432,704, dated Oct. 30, 2019, 25 pages.

Official Action for U.S. Appl. No. 15/432,704, dated Feb. 4, 2020, 26 pages.

Official Action for U.S. Appl. No. 15/432,704, dated May 13, 2020, 21 pages.

Official Action for U.S. Appl. No. 15/432,704, dated Sep. 18, 2020, 21 pages.

(56) References Cited

OTHER PUBLICATIONS

Official Action for U.S. Appl. No. 15/432,704, dated Feb. 24, 2021, 30 pages.
Official Action for U.S. Appl. No. 15/432,704, dated Jul. 28, 2021, 27 pages.
Official Action for U.S. Appl. No. 15/432,704, dated Oct. 28, 2021, 32 pages.
Official Action for U.S. Appl. No. 15/432,704, dated Dec. 17, 2021, 29 pages.
Official Action for U.S. Appl. No. 17/163,896, dated Nov. 23, 2022, 28 pages.
Official Action for U.S. Appl. No. 17/163,896, dated May 12, 2023, 29 pages.
Official Action for U.S. Appl. No. 17/163,896, dated Aug. 24, 2023, 32 pages.
Official Action for U.S. Appl. No. 17/163,896, dated Dec. 27, 2023, 31 pages.
Official Action for U.S. Appl. No. 17/163,896, dated May 28, 2024, 42 pages.
Official Action for U.S. Appl. No. 17/163,896, dated Oct. 18, 2024, 45 pages.
Coric MD, D., et al. Percutaneous, Navigated Minimally Invasive Posterior Cervical Pedicle Screw Fixation. International Journal of Spine Surgery, vol. 14, Supplement 3, 2020, pp. S14-S21.
Domagoj Coric, MD1, and Vincent Rossi, MD, MBA. Percutaneous Posterior Cervical Pedicle Instrumentation (C1 to C7) With Navigation Guidance: Early Series of 27 Cases. Global Spine Journal 2022, vol. 12(2S) 27S-33S.
Official Action for U.S. Appl. No. 18/076,766, dated May 23, 2025, 15 pages.

* cited by examiner

SPINAL IMPLANT SYSTEM AND METHOD

CROSS REFERENCE TO RELATED APPLICATIONS

This application is a continuation of U.S. patent application Ser. No. 17/976,163, filed Oct. 28, 2022, which is expressly incorporated by reference herein, in its entirety.

TECHNICAL FIELD

The present disclosure generally relates to medical devices for the treatment of musculoskeletal disorders, and more particularly to a spinal implant system and a method for treating a spine.

BACKGROUND

Spinal pathologies and disorders such as kyphosis, scoliosis and other curvature abnormalities, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs including vertebral rods are often used to provide stability to a treated region. Rods redirect stresses away from a damaged or defective region while healing takes place to restore proper alignment and generally support vertebral members. During surgical treatment, one or more rods and bone fasteners can be delivered to a surgical site. The rods may be attached via the fasteners to the exterior of two or more vertebral members. Surgical treatment may employ surgical instruments and implants that are manipulated for engagement with vertebrae to position and align one or more vertebrae. This disclosure describes an improvement over these prior technologies.

SUMMARY

In one embodiment, a spinal implant is provided. The spinal implant includes a receiver having a first arm connected to a first extension and a second arm connected to a second extension. The arms are connected to the extensions via a break away surface. The arms include a proximal most end surface and the receiver includes an implant receiving surface. The proximal most end surface and the implant receiving surface define an implant cavity. The break away surface is disposed within the implant cavity. In some embodiments, systems, spinal constructs and methods are disclosed.

In one embodiment, a bone fastener is provided. The bone fastener includes a receiver having a first arm connected to a first extension and a second arm connected to a second extension. The arms are connected to the extensions via a break away surface. The arms include a proximal most end surface, and the receiver includes an implant receiving surface. The proximal most end surface and the implant receiving surface define an implant cavity. The break away surface is disposed within the implant cavity, and a threaded shaft is connectable with the receiver and engageable with vertebral tissue.

In one embodiment, the spinal implant includes a receiver having a first arm connected to a first extension and a second arm connected to a second extension. The arms are connected to the extensions via a break away surface. The receiver includes an inner surface having a selected thread configuration extending along at least a portion of the arms and the extensions. The break away surface includes a helical configuration and is aligned with the thread configuration.

BRIEF DESCRIPTION OF THE DRAWINGS

The present disclosure will become more readily apparent from the specific description accompanied by the following drawings, in which.

DETAILED DESCRIPTION

Figure 1:
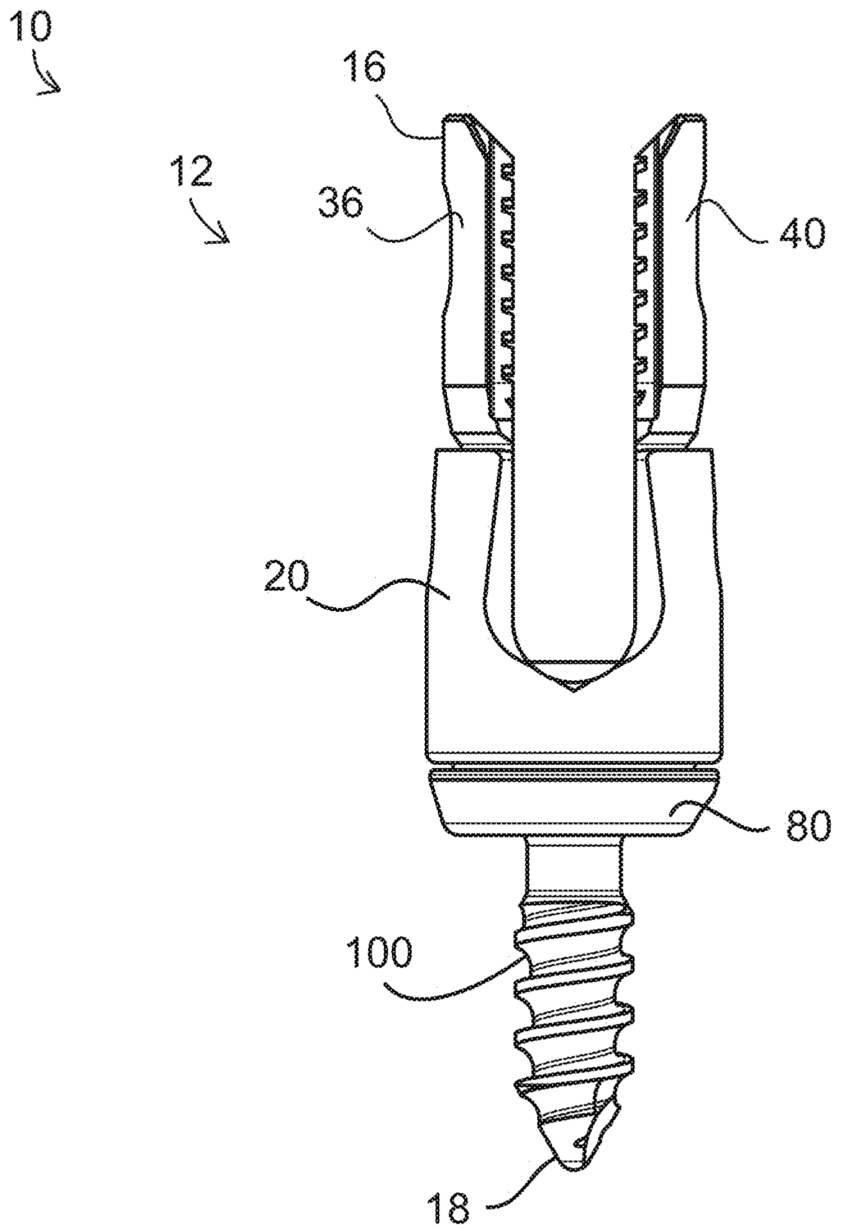
FIG. 1 is a plan view of components of one embodiment of a spinal implant system in accordance with the principles of the present disclosure.

The exemplary embodiments of the surgical system and related methods of use disclosed are discussed in terms of medical devices for the treatment of musculoskeletal disorders and more particularly, in terms of a spinal implant system and a method for treating a spine. In some embodiments, the present surgical system includes a spinal implant including a reduction multi-axial bone fastener having extensions, for example, extender tabs configured to break away, for example, fracture from a receiver of the bone fastener to enable a minimally invasive surgical procedure. In some embodiments, the extensions fracture from the receiver via an undercut. In some embodiments, the extensions fracture from the receiver via a helical cut surface aligned with an internal thread of the receiver. In some embodiments, the present surgical system is implemented in a method for a minimally invasive cervical spinal surgery that includes navigation and/or robotics to enable a surgeon to precisely fix bone fasteners including pedicle bone fasteners and/or lateral mass bone fasteners at a surgical site. In some embodiments, the systems and methods of the present disclosure include medical devices including surgical instruments and implants that are employed with a surgical treatment, as described herein, for example, with a cervical, thoracic, lumbar and/or sacral region of a spine.

In some embodiments, the present surgical system includes a spinal implant including a reduction multi-axial bone fastener having a pair of extensions. In some embodiments, the present surgical system includes a spinal rod configured for fixation with the bone fastener. In some embodiments, the extensions facilitate capture of the spinal rod with the bone fastener. In some embodiments, the extensions are configured to break away, for example, fracture from a receiver of the bone fastener after spinal rod fixation. In some embodiments, the extensions fracture from the receiver via a selected surface geometry to control the location and consistency of the fracture to minimize damage to surrounding tissue at the surgical site.

In some embodiments, the present surgical system includes a reduction multi-axial bone fastener configured for use in a surgical procedure including a minimally invasive spinal deformity procedure. In some embodiments, the bone fastener is employed as a component of a posterior construct. In some embodiments, the present surgical system includes a spinal rod configured for fixation with the bone fastener. In some embodiments, the spinal rod is configured for fixation with an implant receiving surface of the bone fastener. In some embodiments the implant receiving surface includes a portion of a saddle. In some embodiments, a pair of extensions connected to a receiver of the bone fastener are configured to capture the spinal rod with the bone fastener. In some embodiments, a setscrew is configured to fix the spinal rod with the bone fastener. In some embodiments, the extensions are configured to break away, for example, fracture from the receiver after spinal rod fixation with the bone fastener. In some embodiments, the extensions are fractured at a recessed surface. In some embodiments, the recessed surface includes an undercut. In some embodiments, the recessed surface includes a helix configuration. In some embodiments, the recessed surface is configured to reduce the amount of soft tissue surrounding the surgical site that is exposed to the fractured recessed surface. In some embodiments, reduction of soft tissue exposure to the fractured surface can reduce detrimental long term effects in, for example, the cervical spine, where screw-to-skin distance is shallow. In some embodiments, the recessed surface is a selected geometry to control the location and consistency of the resulting fracture surface thereby minimizing the negative impact to surrounding soft tissue.

In some embodiments, the present surgical system includes a bone fastener including a cervical reduction multi-axial bone fastener. In some embodiments, the bone fastener is configured for fixation to the occiput and one or more vertebra, including the T3 vertebra. In some embodiments, the present surgical system includes a plurality of multi-axial bone fasteners, a plurality of hooks, a plurality of cross connectors, a plurality of rod-to-rod connectors and/or a plurality of spinal rods. In some embodiments, the spinal rods are a selected size including 3.2 and/or 3.5 mm. In some embodiments, the spinal rods are a selected size including 4.75 mm, 5.5 mm and/or 6.0 mm. In some embodiments, the spinal rods are manufactured from a titanium alloy and/or a cobalt-chrome alloy.

In some embodiments, the present surgical system includes a cervical reduction multi-axial bone fastener. In some embodiments, the bone fastener includes a pair of extensions. In some embodiments, the extensions are configured to fracture from a surface of a receiver of the bone fastener via a selected geometry, for example, a fracture surface including an undercut. In some embodiments, the undercut is recessed beneath a shoulder of the receiver, for example, beneath a saddle or a crown of the bone fastener. In some embodiments, the undercut forms a shroud around a perimeter of a surface that forms when the extensions break off and reduces potential contact and/or injury to the surrounding soft tissue. In some embodiments, the undercut includes an internal thread and a helical cut on an outer surface of the receiver aligned with a specific thread on an inner surface of the receiver to produce a shear point. In some embodiments, the helical cut can be implemented as visual inspection to a user and is a low-cost approach of facilitating a repeatable break-off zone on the bone fastener. In some embodiments, the shear point includes a shear ring. In some embodiments, the shear point is configured to facilitate removal of the extensions when a force is applied to the extensions. In some embodiments, the force is applied manually to the extensions. In some embodiments, the formation of shear points can be applied to cervical bone fasteners and can be applied to bone fasteners implemented in thoracolumbar deformity procedures. In some embodiments, the recessed shoulder and the helical cut are manufactured from wrought 90% titanium, 6% aluminum, 4% vanadium, 0.25% (max) iron and 0.2% (max) oxygen (Ti-6Al-4V). In some embodiments, all or a portion of the bone fastener is manufactured from Ti-6Al-4V. In some embodiments, the bone fastener is manufactured from 3D printing. In some embodiments, the bone fastener is manufactured from 3D printing utilizing Ti-6Al-4V powder.

In some embodiments, a method for using a surgical system, including multi-axial bone fasteners is provided. In some embodiments, the method includes a minimally invasive cervical spinal surgery that includes navigation and robotics to enable a surgeon to precisely fix bone fasteners including pedicle bone fasteners and lateral mass bone fasteners to a surgical site. In some embodiments, the bone fastener system includes pedicle bone fasteners. In some embodiments, the bone fasteners include cervical reduction bone fasteners including extensions that are connected with extenders. In some embodiments, the bone fasteners are connected to extenders, caps and selected instrumentation to enable minimally invasive thoracolumbar spinal surgery. In some embodiments, the selected instrumentation includes a surgical driver. In some embodiments, the driver is configured to fix the bone fastener with a surgical site. In some embodiments, the surgical system is configured for fixation of the occiput and the T3 vertebra.

In some embodiments, a method for a minimally invasive surgical procedure is provided that includes the present surgical system as described herein. In some embodiments, the method includes the step of attaching extenders to the extensions. In some embodiments, attaching the extenders to the extensions enables a surgeon to position the bone fasteners using navigation such that small incisions can be created and enables access to the bone fasteners below skin of a patient. In some embodiments, the method includes the step engaging a cap to a top end of the extenders. In some embodiments, engaging the cap to the top end of the extenders provides stability and is configured to align instruments with bone fastener threads. In some embodiments, the method includes the step of inserting the bone fastener attached to the extenders and cap into a surgical site. In some embodiments, the surgical site includes cervical vertebrae each having a pedicle. In some embodiments, the method includes the step of engaging a spinal rod with the extensions. In some embodiments, the method includes the step of translating a setscrew through the caps and extenders with a surgical instrument and into a receiver of the bone fastener to engage the spinal rod with the bone fastener. In some embodiments, the surgical instrument includes a driver. In some embodiments, the method includes the step of tightening the set screw within the receiver to fix the spinal rod with the bone fastener. In some embodiments, the method includes the step of removing the cap from the extenders. In some embodiments, the method includes the step of sliding an instrument over the extensions and the extenders, and rocking the instrument to break the extensions from the bone fastener. In some embodiments, break-off portions of the extensions are manufactured such that when the extensions are broken, a top of the receiver is flat and the broken portion is located below the top of the receiver.

In some embodiments, the surgical system of the present disclosure may be employed to treat spinal disorders, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including a spinal implant, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-15, there are illustrated components of a surgical system, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, for example, composites of metals and calcium-based ceramics, composites of PEEK and calcium based ceramics, composites of PEEK with resorbable polymers, totally resorbable materials, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a fully open surgical procedure, a minimally invasive procedure including percutaneous techniques, and mini-open surgical techniques to deliver and introduce instrumentation and/or a spinal implant, for example, a bone fastener, at a surgical site of a patient, which includes, for example, a spine. In some embodiments, the spinal implant can include one or more components of one or more spinal constructs, for example, interbody devices, interbody cages, bone fasteners, spinal rods, tethers, connectors, plates and/or bone graft, and can be employed with various surgical procedures including surgical treatment of a cervical, thoracic, lumbar and/or sacral region of a spine.

Figure 2:
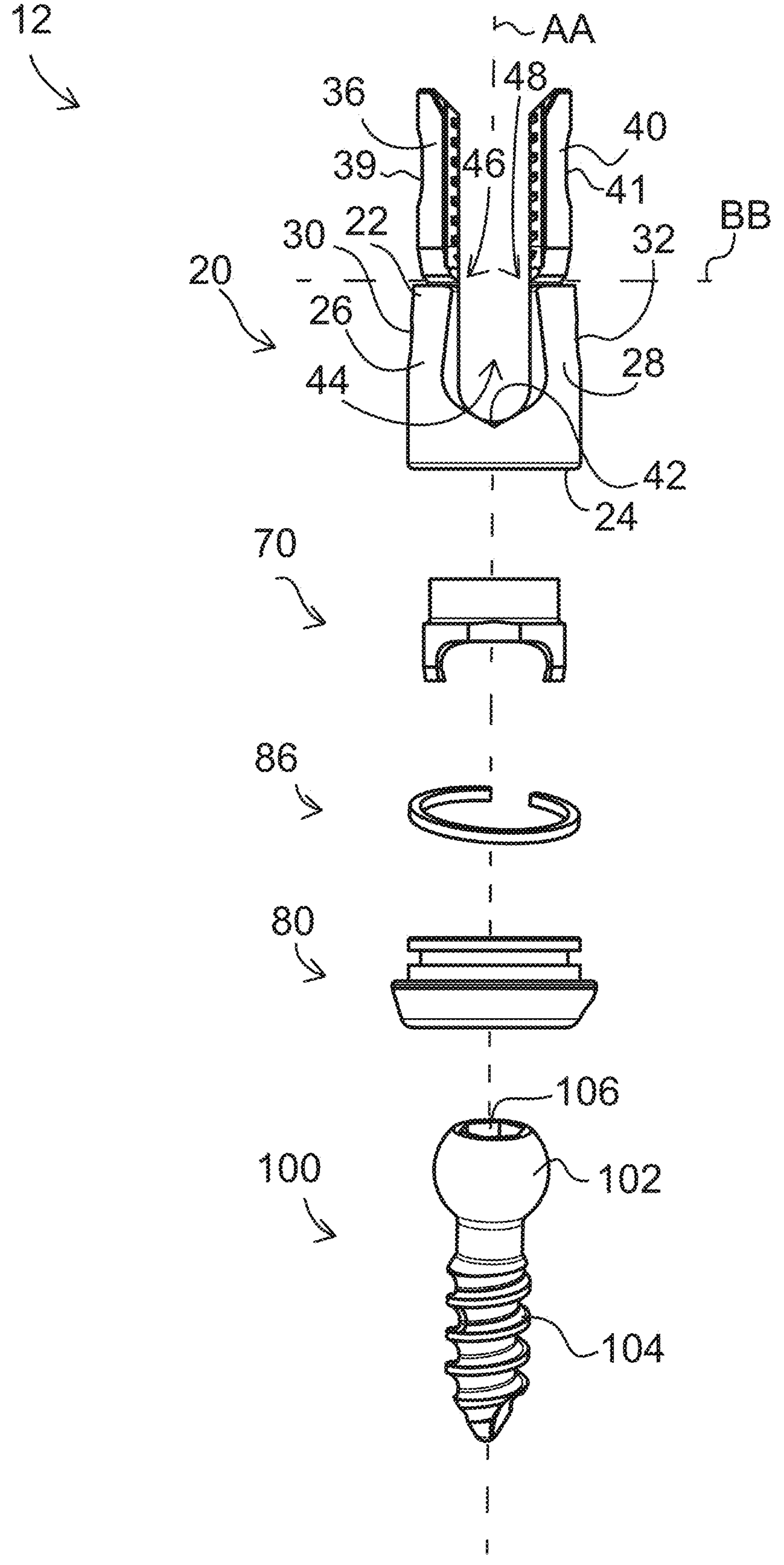
FIG. 2 is a plan view of the components shown in FIG. 1 with parts separated.
Figure 3:
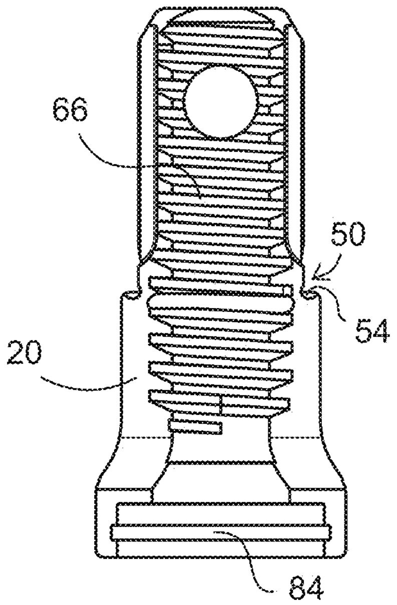
FIG. 3 is a cross section view of the receiver component of the system shown in FIG. 1.
Figure 4:
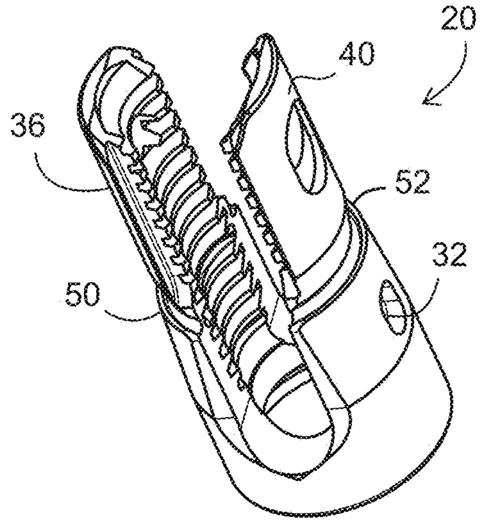
FIG. 4 is a perspective view of the receiver component shown in FIG. 1.

Spinal implant system 10 includes a spinal implant, for example, a bone fastener 12, as shown in FIGS. 1 and 2. Bone fastener 12 is configured for fixation with a surgical site including vertebral tissue and is configured to receive a spinal implant, for example, a spinal rod 14. Bone fastener 12 extends between an end 16, an end 18 and defines a longitudinal axis AA.

Bone fastener 12 includes a receiver 20 that extends between a proximal end 22 and a distal end 24. End 22 includes an arm 26 and an arm 28. Arms 26, 28 each extend parallel to axis AA. Arms 26, 28 each include an arcuate outer surface extending between a pair of side surfaces. At least one of the outer surfaces and the side surfaces of arms 26, 28 have at least one recess or cavity 30, 32 therein, configured to receive an insertion tool, compression instrument and/or instruments for inserting and tensioning bone fastener 12.

Figure 5:
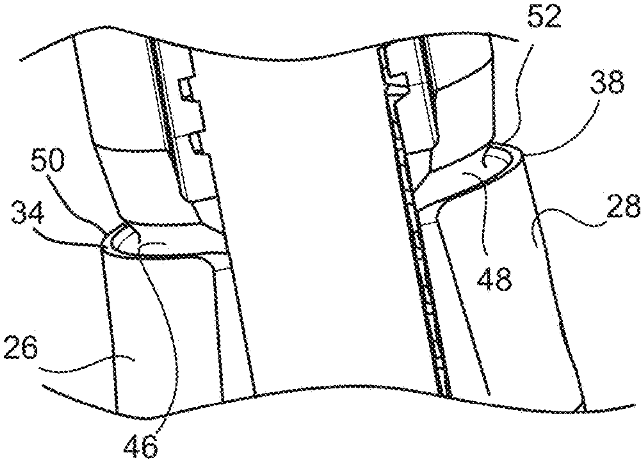
FIG. 5 is a break away view of the receiver component of the system shown in FIG. 1.

Arm 26 includes a proximal most end surface 34, as shown in FIG. 5, configured for connection with an extension 36. Arm 28 includes a proximal most end surface 38 configured for connection with an extension 40. Proximal most end surfaces 34, 38 define a transverse plane BB (FIG. 2) relative to longitudinal axis AA. Extensions 36, 40 each include an arcuate outer surface extending between a pair of side surfaces. At least one of the outer surfaces and the side surfaces of extensions 36, 40 have at least one recess or cavity 39, 41 therein, configured to receive an insertion tool, an extender tab, compression instrument and/or instruments for inserting and tensioning bone fastener 12. In some embodiments, extensions 36, 40 include extender tabs.

Receiver 20 includes an implant receiving surface 42. Implant receiving surface 42 is configured for engagement with surfaces of spinal rod 14. Implant receiving surface 42 includes a saddle 70, as described herein. Proximal most end surfaces 34, 38 and implant receiving surface 42 define an implant cavity 44. In some embodiments, cavity 44 may have various cross section configurations, for example, oval, oblong, triangular, rectangular, square, polygonal, irregular, uniform, non-uniform, variable and/or tapered.

Arm 26 is connected to extension 36 via a break away surface 46, and arm 28 is connected to extension 40 via a break away surface 48. Break away surfaces 46, 48 are disposed within cavity 44 and at least a portion of break away surfaces 46, 48 are axially spaced from transverse plane BB. In some embodiments, break away surfaces 46, 48 are connected to proximal most end surfaces 34, 38. In some embodiments, break away surfaces 46, 48 are spaced and separate from proximal most end surfaces 34, 38. Break away surfaces 46, 48 are configured to fracture and separate at a predetermined force or torque limit, described herein. Break away surfaces 46, 48 are configured to fracture and separate from receiver 20 to enable a minimally invasive surgical procedure, described herein. Break away surfaces 46, 48 are configured to control the location and consistency of the resulting fracture surface thereby minimizing the negative impact to soft tissue surrounding bone fastener 12.

Figure 6:
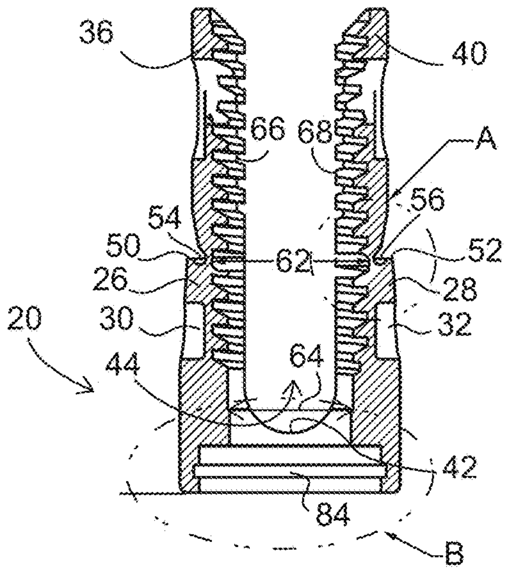
FIG. 6 is a cross section view of the receiver component of the system shown in FIG. 1.
Figure 7:
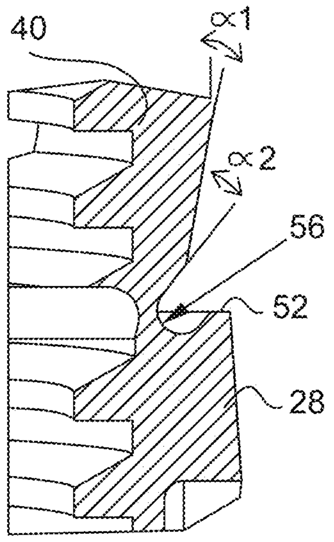
FIG. 7 is a break away view of the components shown in detail A in FIG. 6.

Arm 26 defines a proximal shoulder 50 including proximal most end surface 34, and arm 28 defines a proximal shoulder 52 including proximal most end surface 38, as shown in FIGS. 3-7. Break away surface 46 includes an undercut 54 being recessed within proximal shoulder 50, and break away surface 48 includes an undercut 56 being recessed within proximal shoulder 52. Undercuts 54, 56 are configured to form a shroud about a perimeter of shoulders 50, 52 when extensions 36, 40 fracture and separate from receiver 20, thereby reducing potential contact and/or injury to soft tissue surrounding bone fastener 12. In some embodiments, a portion of extensions 36, 40 include an angle $\alpha\mathbf{1}$, and undercuts 54, 56 include an angle $\alpha\mathbf{2}$, as shown in FIG. 7. In some embodiments, angle $\alpha\mathbf{1}$ includes an angle in a range of 10 to 30 degrees relative to longitudinal axis AA. In some embodiments, angle $\alpha\mathbf{2}$ includes an angle in a range of 60 to 90 degrees relative to longitudinal axis AA. In some embodiments, angle $\alpha\mathbf{1}$ includes an angle in a range of 20 degrees and angle $\alpha\mathbf{2}$ includes an angle of 75 degrees.

Figure 11:
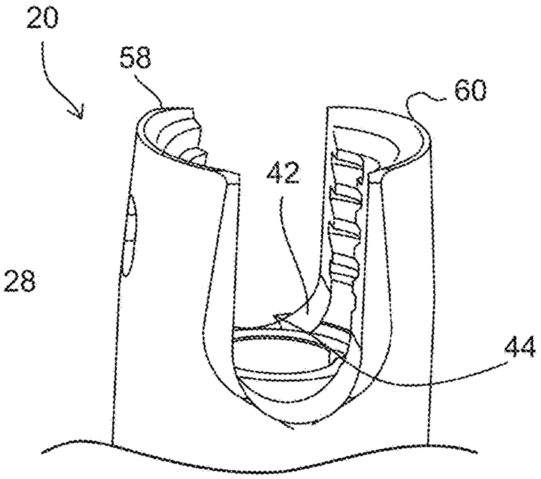
FIG. 11 is a break away view of the components shown in FIG. 10.

Break away surface 46 includes a circumferential wall 58 configured to connect arm 26 to extension 36, and break away surface 48 includes a circumferential wall 60 configured to connect arm 28 to extension 40, as shown in FIG. 11. Walls 58, 60 are fabricated from a fracturing and/or frangible material such that manipulation of extensions 36, 40 can fracture and separate extensions 36, 40 from arms 26, 28 at a predetermined force and/or torque limit, as described herein. Walls 58, 60 have a reduced thickness relative to extensions 36, 40 to facilitate fracture and separation. In some embodiments, walls 58, 60 form a shear point, for example, a shear ring to facilitate fracture and separation.

Break away surfaces 46, 48 are configured to fracture and separate at a predetermined force or torque limit. In some embodiments, the predetermined force or torque limit includes a range of approximately 2 to 8 Nm. In some embodiments, extensions 36, 40 and arms 26, 28 may have the same or alternate cross section configurations, may be fabricated from a homogenous material or heterogeneously fabricated from different materials, and/or alternately formed of a material having a greater degree, characteristic or attribute of plastic deformability, frangible property and/or break away quality to facilitate fracture and separation of extensions 36, 40.

Proximal most end surfaces 34, 38 define a proximal boundary 62 of cavity 44 and implant receiving surface 42 defines a distal boundary 64 of cavity 44, as shown in FIG. 6. Receiver 20 includes inner threaded surfaces 66, 68 extending along at least a portion of arms 26, 28 and extensions 36, 40. Inner threaded surfaces 66, 68 are configured for engagement with a set screw (not shown).

Figure 12:
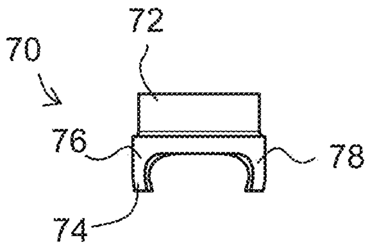
FIG. 12 is a side view of components of the system shown in FIG. 1.
Figure 13:
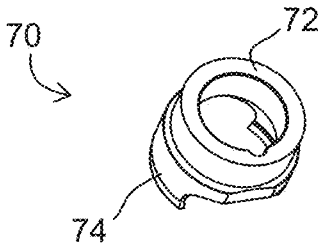
FIG. 13 is a perspective view of components of the system shown in FIG. 1.

Implant receiving surface 42 includes saddle 70, as shown in FIGS. 12-13, configured to receive spinal rod 14. Saddle 70 includes an end 72 and an end 74. End 72 is configured to receive spinal rod 14 and end 74 is configured for engagement with a head 102 of a shaft 100 of bone fastener 12, as described herein. End 74 includes sections 76, 78 configured to contour to head 102.

Figure 8:
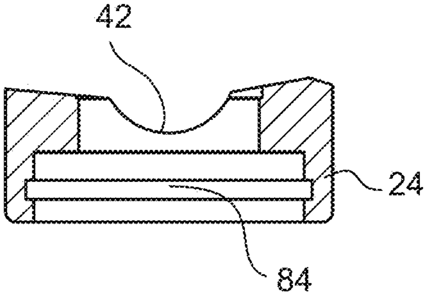
FIG. 8 is a break away view of the components shown in detail B in FIG. 6.
Figure 9:
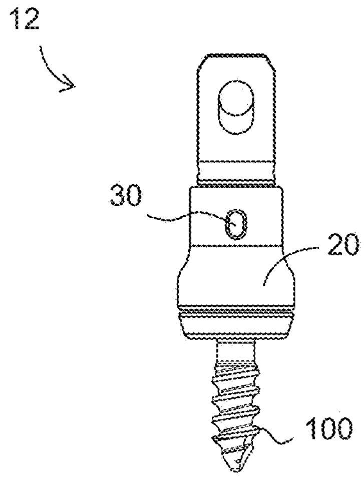
FIG. 9 is a side view of components of the system shown in FIG. 1.
Figure 10:
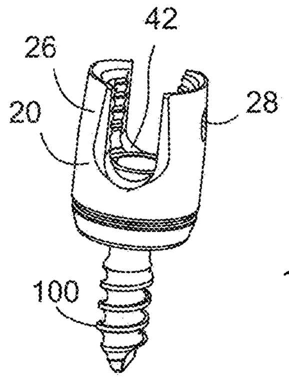
FIG. 10 is a perspective view of components of the system shown in FIG. 1.
Figure 14:
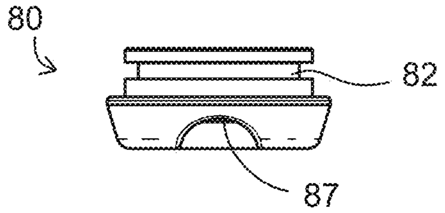
FIG. 14 is a side view of components of the system shown in FIG. 1.
Figure 15:
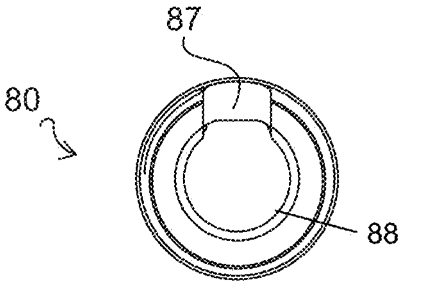
FIG. 15 is a plan view of components of the system shown in FIG. 1.
Figure 16:
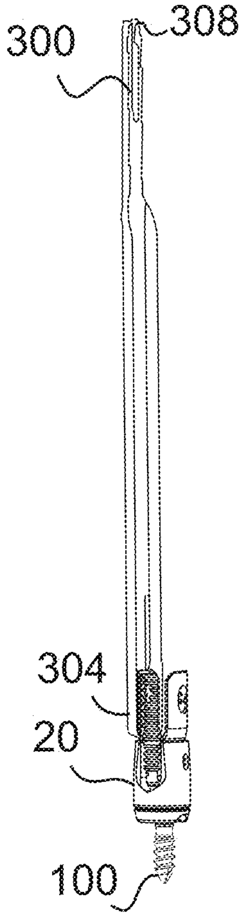
FIG. 16 is a perspective view of components of one embodiment of a spinal implant system in accordance with the principles of the present disclosure.
Figure 17:
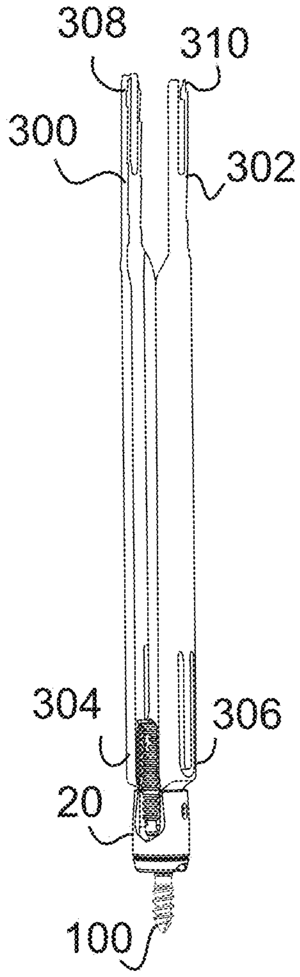
FIG. 17 is a perspective view of components of one embodiment of a spinal implant system in accordance with the principles of the present disclosure.
Figure 18:
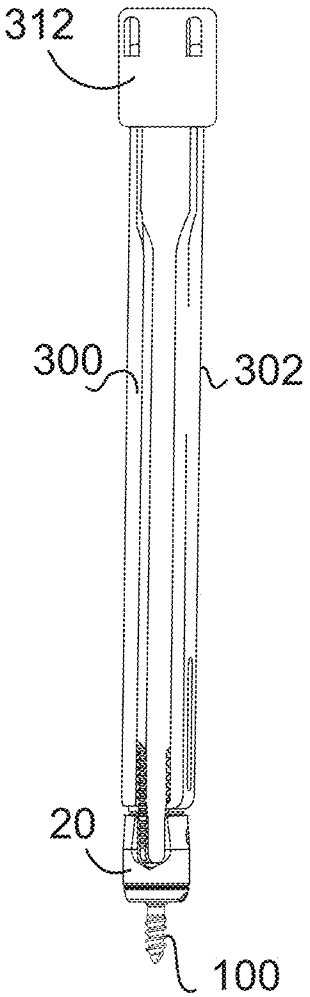
FIG. 18 is a perspective view of components of one embodiment of a spinal implant system in accordance with the principles of the present disclosure.

Bone fastener 12 includes a base 80, as shown in FIGS. 14-15. Base 80 includes a flange 82 configured for connection with groove 84 of receiver 20, as shown in FIGS. 6 and 8, and a ring 86. An outer surface includes an arcuate portion 87. In some embodiments, portion 87 is configured to facilitate hyper-angulation of bone fastener 12. Base 80 includes an inner surface 88 configured for engagement with saddle 70 and head 102.

Shaft 100 includes a threaded portion 104 connectable with receiver 20 and engageable with tissue, for example, vertebral tissue. In some embodiments, threaded portion 104 may include a single thread turn or a plurality of discrete threads. Head 102 includes a tool engaging portion 106 configured to engage a surgical tool or instrument, as described herein. In some embodiments, portion 106 includes a hexagonal cross-section. In some embodiments, head 102 includes an outer surface having planar surfaces or flats and/or arcuate surfaces.

In assembly, operation and use, spinal implant system 10, similar to the systems and methods described herein, is employed with a surgical procedure, for example, treatment of an applicable condition or injury of an affected section of a spinal column and adjacent areas within a body. In some embodiments, one or all of the components of spinal implant system 10 can be delivered or utilized as a pre-assembled device or can be assembled in situ. Spinal implant system 10 may be completely or partially revised, removed or replaced.

In use, to treat vertebrae, for example, cervical vertebrae, patient anatomy is imaged including a surgical site. In some embodiments, patient anatomy is imaged via x-ray images appropriate for a selected surgical procedure. In some embodiments, spinal implant system 10 includes a surgical navigation system including an O-Arm® imaging device sold by Medtronic Navigation, Inc. having a place of business in Louisville, Colo., USA.

A medical practitioner obtains access to the surgical site in any appropriate manner, such as through percutaneous incision and/or retraction of tissues. In some embodiments, spinal implant system 10 can be used in any existing surgical method or technique including open surgery, mini-open surgery, minimally invasive surgery and percutaneous surgical implantation, whereby the vertebrae is accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway, for example, a minimally invasive pathway including a pedicle of cervical vertebrae of the patient anatomy, for implantation of components of spinal implant system 10. In some embodiments, the pathway includes a substantially lateral to medial trajectory of patient anatomy. In some embodiments, the pathway includes a pedicle of a first cervical vertebrae and a lateral mass of a second cervical vertebrae. A preparation instrument (not shown) can be employed to prepare tissue surfaces of the vertebrae as well as for aspiration and irrigation of a surgical region.

Cavities, for example, pilot holes (not shown) are created with a surgical instrument, for example, a surgical drill and/or a surgical tap, in selected levels of vertebrae, for example, at least a portion of pedicles of the vertebrae for receiving shafts 100 of bone fasteners 12. A surgical instrument, for example, a driver is connected with bone fasteners 12 and bone fasteners 12 are engaged with vertebrae. In some embodiments, bone fasteners 12 are engaged in a trans articular fixation of a first cervical vertebra and a second cervical vertebra. In some embodiments, bone fasteners 12 are engaged in a trans articular fixation of a first cervical vertebra and a first thoracic vertebra.

Figure 19:
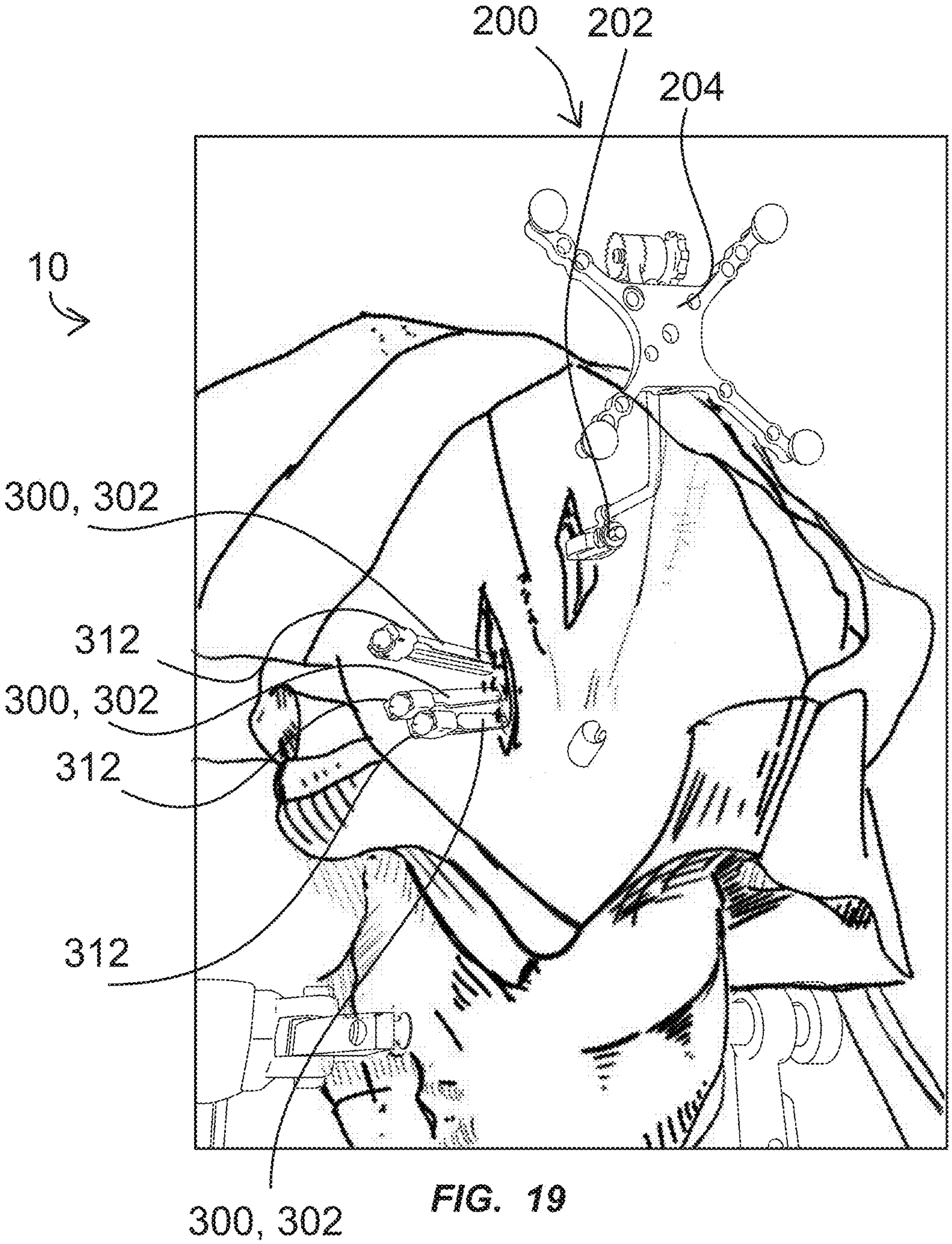
FIG. 19 is a perspective view of components of one embodiment of a spinal implant system in accordance with the principles of the present disclosure disposed with an anatomy.
Figure 20:
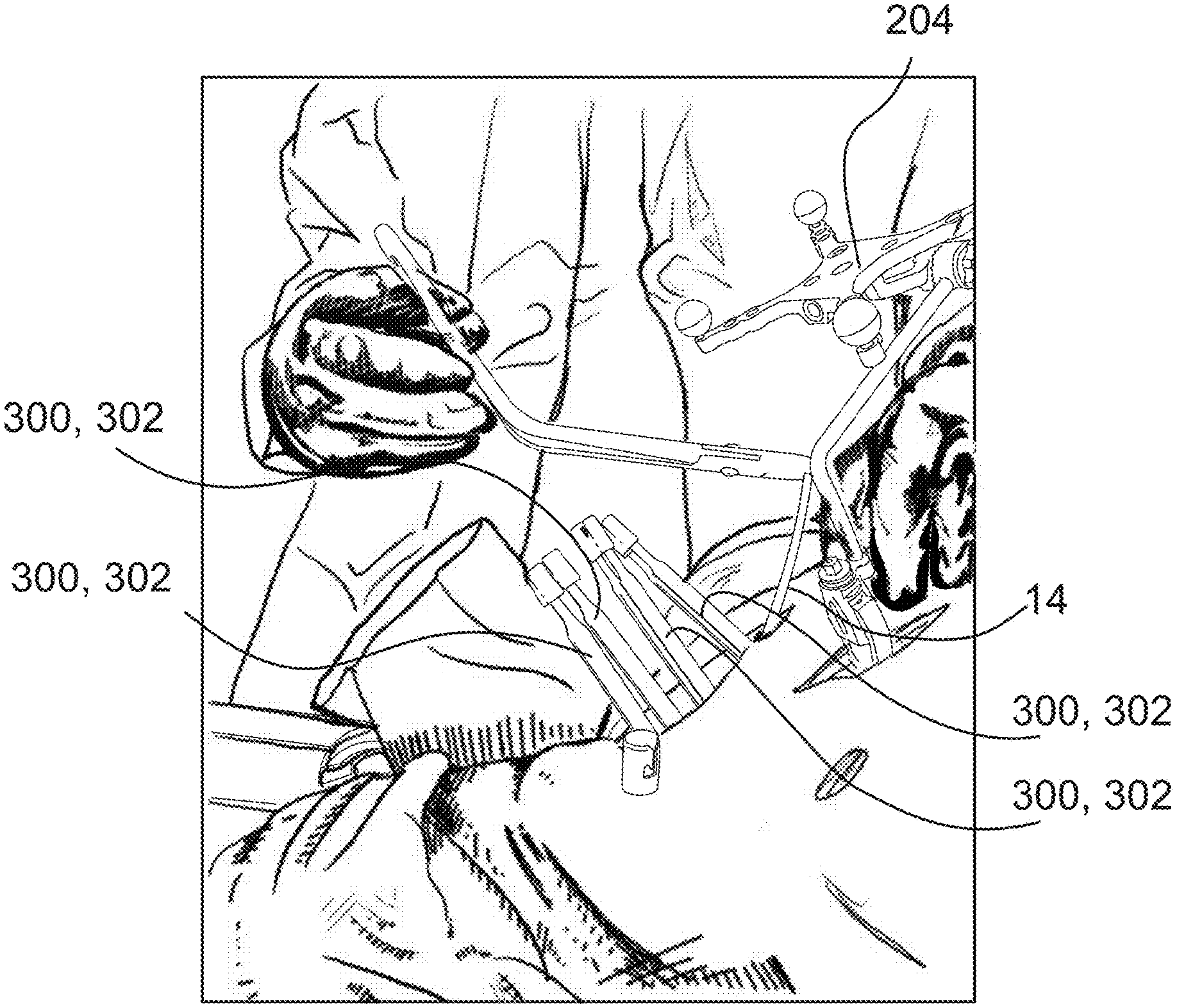
FIG. 20 is a perspective view of components of one embodiment of a spinal implant system in accordance with the principles of the present disclosure disposed with an anatomy.
Figure 21:
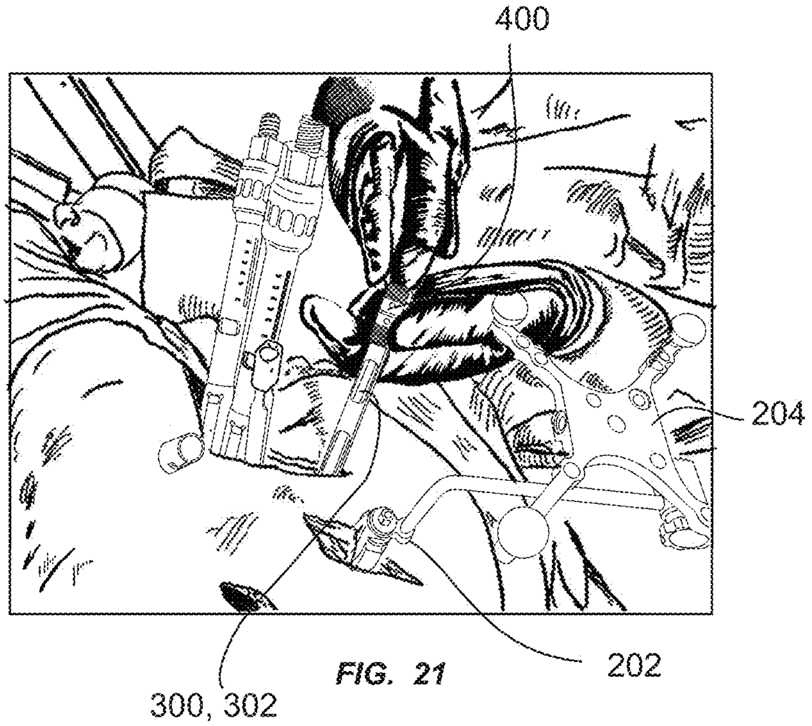
FIG. 21 is a perspective view of components of one embodiment of a spinal implant system in accordance with the principles of the present disclosure disposed with an anatomy.
Figure 22:
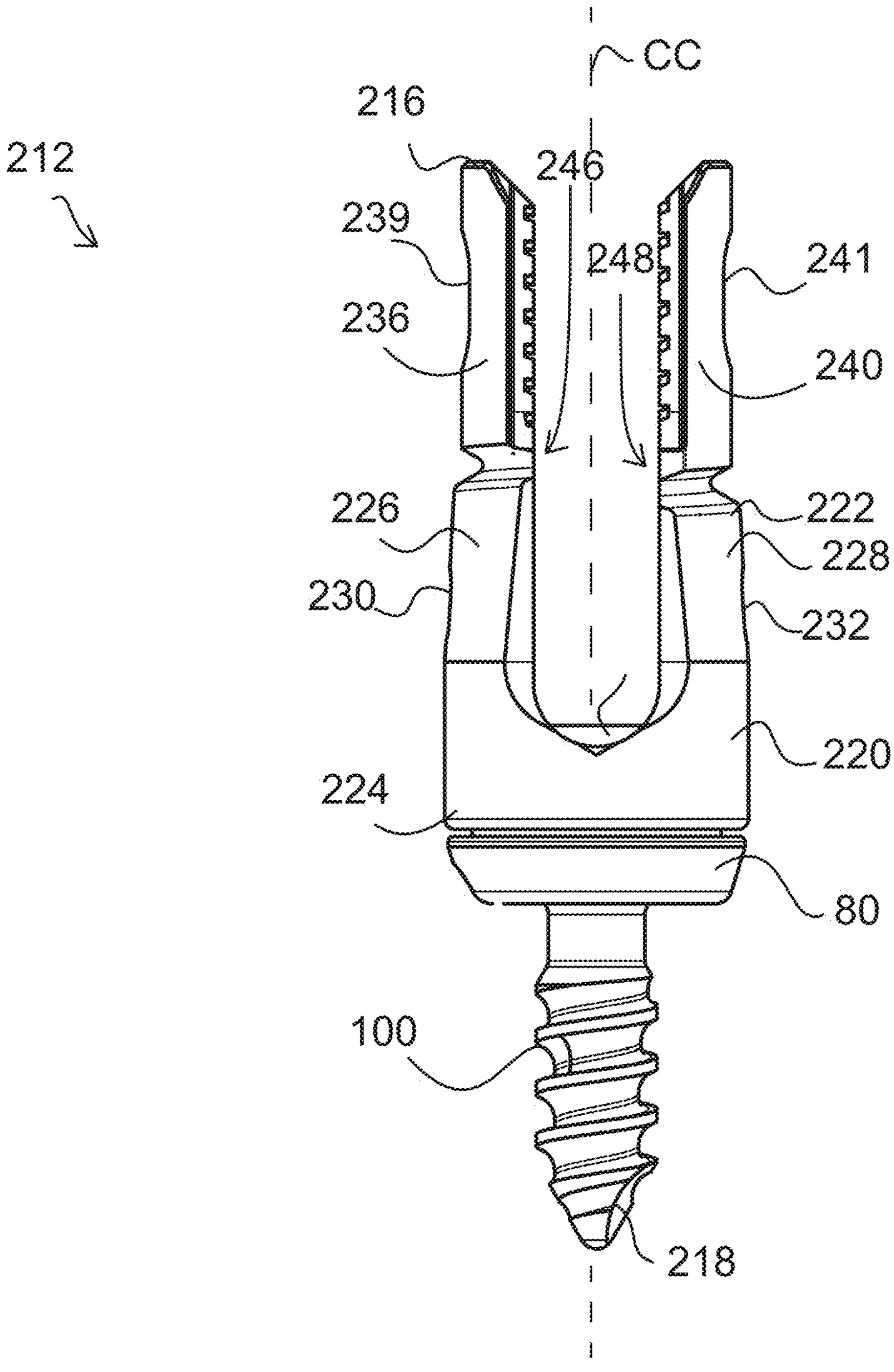
FIG. 22 is a plan view of components of one embodiment of a spinal implant system in accordance with the principles of the present disclosure.
Figure 23:
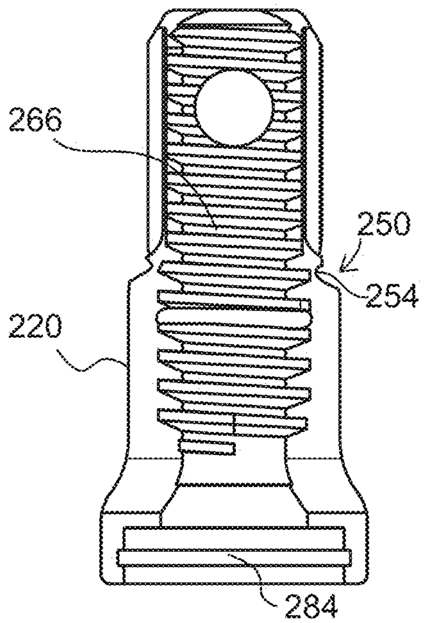
FIG. 23 is a cross section view of the receiver component of the system shown in FIG. 22.
Figure 24:
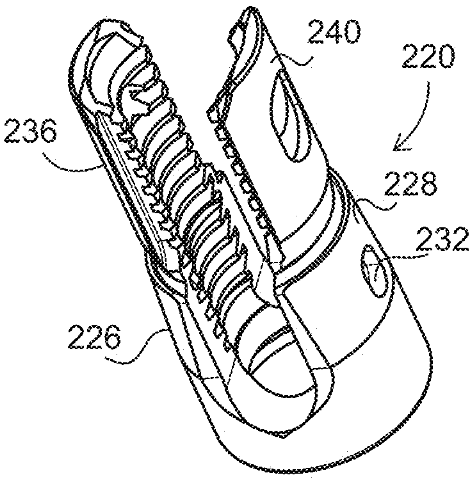
FIG. 24 is a perspective view of the receiver component of the system shown in FIG. 22.

In some embodiments, the surgical instruments include a surgical navigation component 200 (FIG. 19) which generates a signal representative of a position of the surgical instruments and/or bone fasteners 12 relative to the surgical site. In some embodiments, during creation of the cavities, a guide member 202 is disposed with the patient anatomy. In some embodiments, guide member 202 is configured for disposal with the surgical instrument(s) and an image guide 204 is oriented relative to a sensor (not shown) to communicate a signal representative of a position of guide member 202. In some embodiments, guide member 202 includes an end effector of a robotic arm. In some embodiments, surgical navigation component 200 includes a tracking device (not shown) including a sensor (not shown) that receives the signal and communicates with a processor (not shown) to generate data for display of an image from a monitor (not shown). In some embodiments, the image represents a position of guide member 202 relative to the surgical site. In some embodiments, the tracking device includes an EM tracking system that can include the STEALTHSTATION® AXIEM™ Navigation System, sold by Medtronic Navigation, Inc. having a place of business in Louisville, Colo. Exemplary tracking systems are also disclosed in U.S. Pat. Nos. 8,057,407, 5,913,820, and 5,592,939, the entire contents of each of these references being incorporated by reference herein.

Ends 304, 306 of extenders 300, 302 are connected with bone fasteners 12 via extensions 36, 40, as shown in FIGS. 16-18 and 20-21. A cap 312 is disposed at ends 308, 310 of extenders 300, 302 to retain extenders 300, 302. In some embodiments, extenders 300, 302 are configured to facilitate bone fasteners 12 placement using navigation to make small incisions in the patient and enables the surgeon to have access to bone fasteners 12 below the skin of the patient. In some embodiments, cap 312 is configured to provide stability to extenders 300, 302, and extenders 300, 302 are configured to align instruments described herein with bone fasteners 12.

Spinal rod 14 is delivered along the surgical pathway for connection with one or more bone fasteners 12. Spinal rod 14 is translated through extensions 36, 40 of each bone fastener 12. Setscrews (not shown) are translated through caps 312 and extensions 36, 40, and the setscrews are threaded in a direction, for example, a downward direction until spinal rod 14 is fixed with bone fasteners 12. Spinal rod 14 is fully seated within bone fasteners 12, the setscrews are fully tightened and cap 312 is removed from extenders 300, 302. A surgical instrument 400 engages over extenders 300, 302 and extensions 36, 40 are rocked back and forth, thereby fracturing and separating extensions 36, 40 from receivers 20 of bone fasteners 12. Undercuts 54, 56 of bone fasteners 12 are configured to form a shroud about a perimeter of shoulders 50, 52 when extensions 36, 40 fracture and separate from receiver 20, thereby reducing potential contact and/or injury to soft tissue surrounding bone fasteners 12.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiomarkers may be included for identification under x-ray, fluoroscopy, CT or other imaging techniques. In some embodiments, spinal implant system 10 may include one or a plurality of spinal rods, plates, connectors and/or bone fasteners for use with a single vertebral level or a plurality of vertebral levels.

In some embodiments, one or more bone fasteners, as described herein, may be engaged with tissue in various orientations, for example, series, parallel, offset, staggered and/or alternate vertebral levels. In some embodiments, the bone fasteners may comprise multi-axial screws, sagittal adjusting screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In one embodiment, spinal implant system 10 includes an agent, which may be disposed, packed, coated or layered within, on or about the components and/or surfaces of spinal implant system 10. In some embodiments, the agent may include bone growth promoting material, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

In one embodiment, as shown in FIGS. 22-28, spinal implant system 10, similar to the systems and methods described herein, includes a bone fastener 212, similar to bone fastener 12. Bone fastener 212 is configured for fixation to a surgical site including vertebral tissue and is configured to receive spinal rod 14. Bone fastener 212 extends between an end 216, an end 218 and defines a longitudinal axis CC.

Bone fastener 212 includes a receiver 220, similar to receiver 20 described herein. Receiver 220 extends between a proximal end 222 and a distal end 224. End 222 includes an arm 226 and an arm 228, similar to arms 26, 28 described herein. Arms 226, 228 each extend parallel to axis CC. Arms 226, 228 each include an arcuate outer surface extending between a pair of side surfaces. At least one of the outer surfaces and the side surfaces of arms 226, 228 have at least one recess or cavity 230, 232 therein, configured to receive an insertion tool, compression instrument and/or instruments for inserting and tensioning bone fastener 212.

Figure 25:
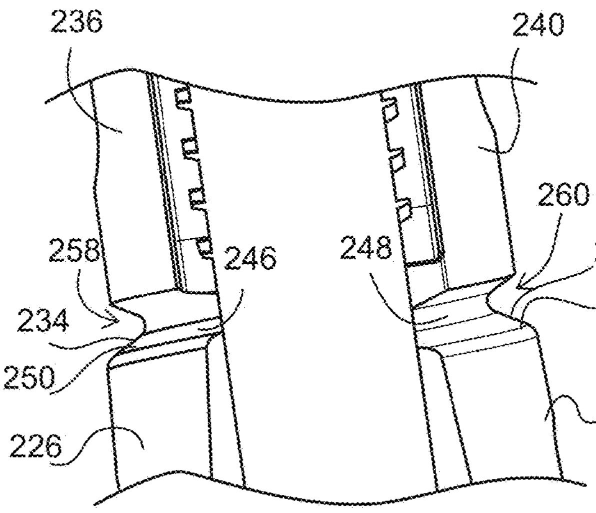
FIG. 25 is a break away view of the receiver component of the system shown in FIG. 22.

Arm 226 includes a proximal end 234, as shown in FIG. 25, configured for connection with an extension 236, similar to extension 36. Arm 228 includes a proximal end 238 configured for connection with an extension 240, similar to extension 40. Extensions 236, 240 each include an arcuate outer surface extending between a pair of side surfaces. At least one of the outer surfaces and the side surfaces of extensions 236, 240 have at least one recess or cavity 239, 241 therein, configured to receive an extender tab, insertion tool, compression instrument and/or instruments for inserting and tensioning bone fastener 12. In some embodiments extensions 236, 240 include extender tabs.

Receiver 220 includes an implant receiving surface 242, similar to implant receiving surface 42 described herein. Implant receiving surface 242 is configured for engagement with surfaces of spinal rod 14. Implant receiving surface 242 includes saddle 70 described herein. Proximal ends 234, 238 and implant receiving surface 242 define an implant cavity 244, similar to cavity 44 described herein.

Arm 226 is connected to extension 236 via a break away surface 246, similar to break away surface 46 described herein. Arm 228 is connected to extension 240 via a break away surface 248, similar to break away surface 48 described herein. Break away surfaces 246, 248 are configured to fracture and separate at a predetermined force or torque limit, described herein. Break away surfaces 246, 248 are configured to fracture and separate from receiver 220 to enable a minimally invasive surgical procedure, described herein. Break away surfaces 246, 248 are configured to control the location and consistency of the resulting fracture surface thereby minimizing the negative impact to soft tissue surrounding bone fastener 212.

Figure 26:
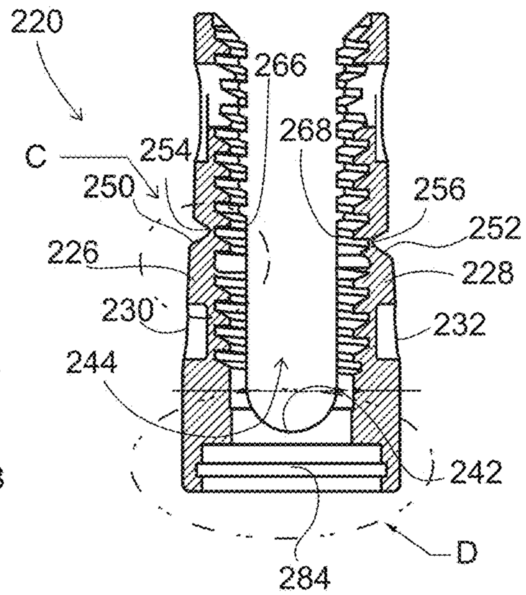
FIG. 26 is a cross section view of the receiver component of the system shown in FIG. 22.
Figure 27:
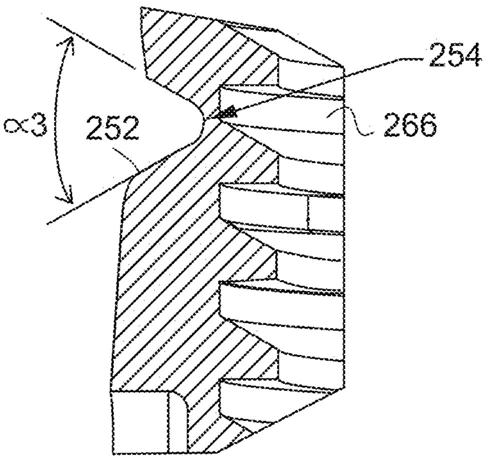
FIG. 27 is a break away view of the components shown in detail C in FIG. 26.
Figure 28:
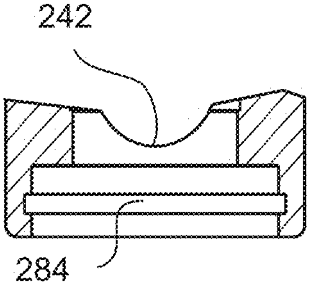
FIG. 28 is a break away view of the components shown in detail D in FIG. 26.

Break away surfaces 246, 248 include a helical configuration and are aligned with a thread configuration of inner surfaces 266, 268 of receiver 220, such that extensions 236, 240 can fracture and separate from receiver 220, as shown in FIGS. 26-27. Inner surfaces 266, 268 extend along at least a portion of arms 226, 228 and extensions 236, 240.

Arm 226 defines a proximal shoulder 250 including proximal end 234, as shown in FIGS. 25 and 26. Arm 228 defines a proximal shoulder 252 including proximal end 238. Break away surface 246 includes a groove 254 and break away surface 248 includes a groove 256. In some embodiments, grooves 254, 256 include an angle $\alpha 3$, as shown in FIG. 27. In some embodiments, angle $\alpha 3$ includes an angle in a range of 40 to 90 degrees relative to longitudinal axis CC. In some embodiments, angle $\alpha 3$ includes an angle of 60 degrees.

Break away surface 246 includes a helical wall 258 configured to connect arm 226 to extension 236, and break away surface 248 includes a helical wall 260 configured to connect arm 228 to extension 240, shown in FIG. 25. Walls 258, 260 are fabricated from a fracturing and/or frangible material such that manipulation of extensions 236, 240 can fracture and separate extensions 236, 240 from arms 226, 228 at grooves 254, 256 that are aligned with the thread configuration of inner surfaces 266, 268 of receiver 220 at a predetermined force and/or torque limit, as described herein and shown in FIGS. 26-27. Walls 258, 260 have a reduced thickness relative to extensions 236, 240 to facilitate fracture and separation.

Break away surfaces 246, 248 are configured to fracture and separate at a predetermined force or torque limit. In some embodiments, the predetermined force or torque limit includes a range of approximately 2 to 8 Nm. In some embodiments, extensions 236, 240 and arms 226, 228 may have the same or alternate cross section configurations, may be fabricated from a homogenous material or heterogeneously fabricated from different materials, and/or alternately formed of a material having a greater degree, characteristic or attribute of plastic deformability, frangible property and/or break away quality to facilitate fracture and separation of extensions 236, 240.

Implant receiving surface 242 includes saddle 70, as described herein, configured to receive spinal rod 14. Bone fastener 212 includes base 80, as described herein, configured for connection with a groove 284 of receiver 220, and ring 86. In some embodiments, base 80 is manually engageable with shaft 100 to connect receiver 220 and shaft 100 in a non-instrumented snap-fit assembly.

Figure 29:
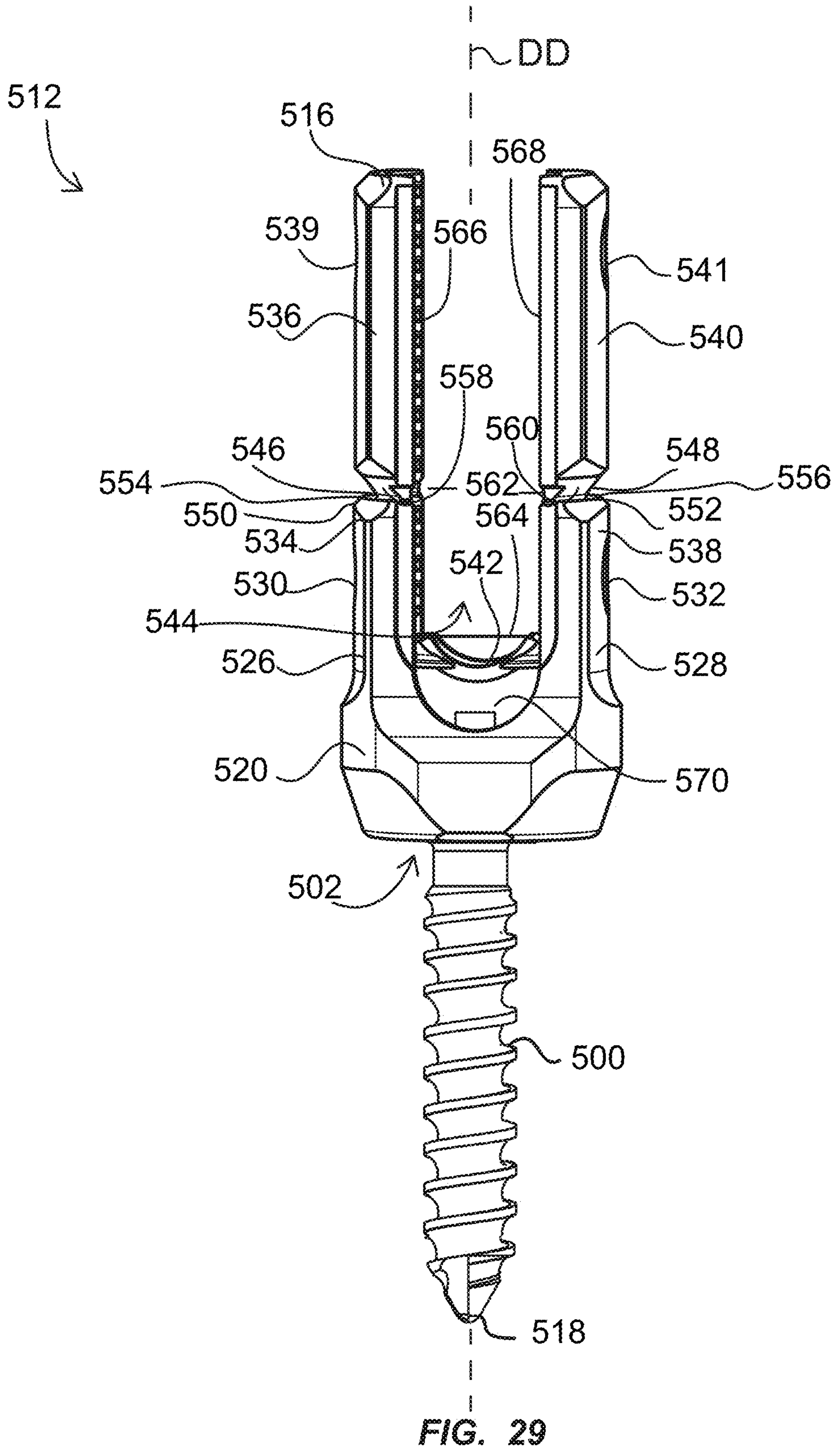
FIG. 29 is a plan view of components of one embodiment of a spinal implant system in accordance with the principles of the present disclosure.
Figure 30:
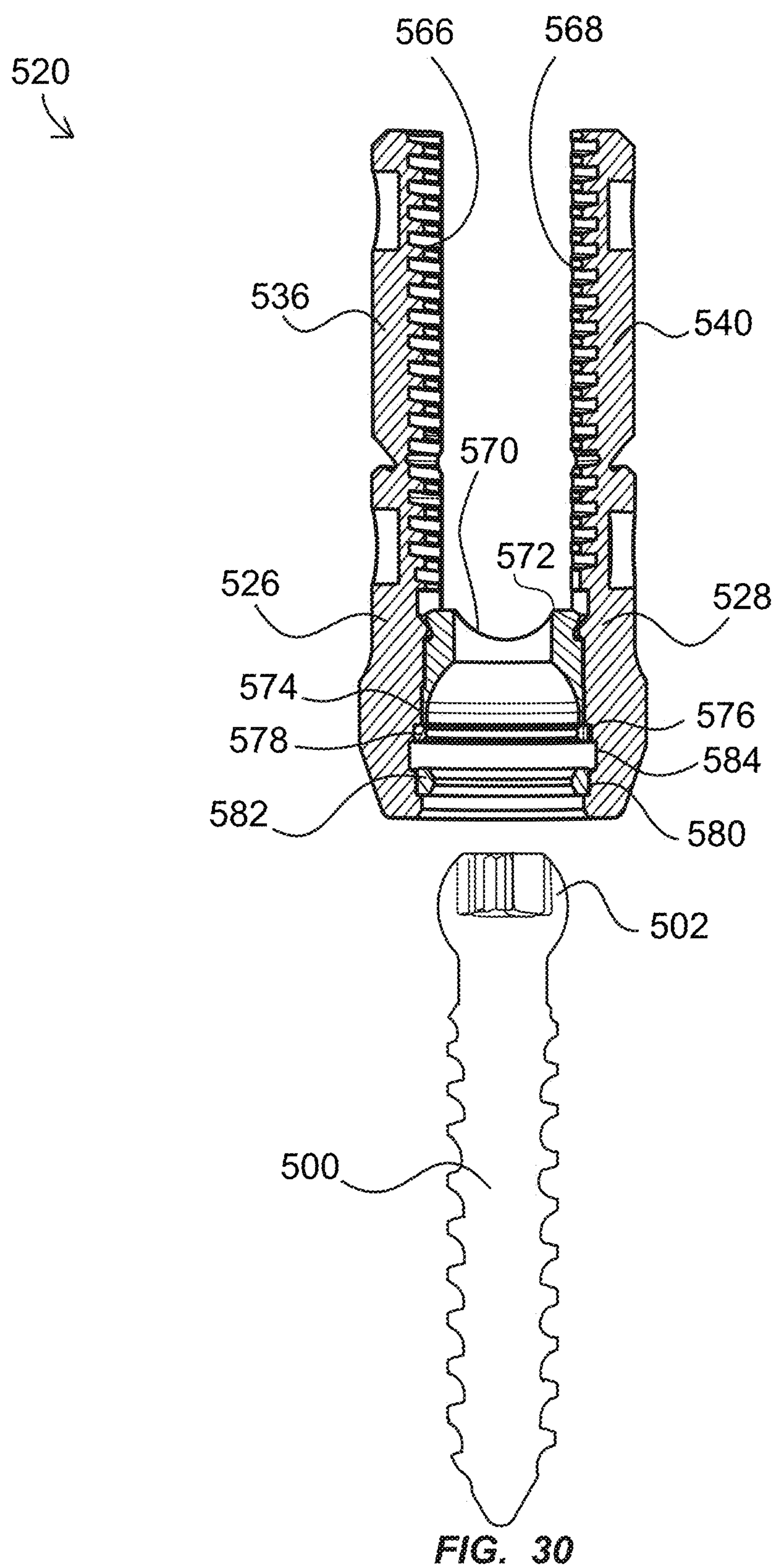
FIG. 30 is a cross section view of components of the system shown in FIG. 29.

In one embodiment, as shown in FIGS. 29-30, spinal implant system 10, similar to the systems and methods described herein, includes a bone fastener 512, similar to bone fastener 12. Bone fastener 512 is configured for fixation to a surgical site including vertebral tissue and is configured to receive spinal rod 14. Bone fastener 512 includes a reduction multi axial screw. Bone fastener 512 extends between an end 516, an end 518 and defines a longitudinal axis DD, as shown in FIG. 29.

Bone fastener 512 includes a receiver 520, similar to receiver 20 described herein. Receiver 520 includes an arm 526 and an arm 528, similar to arms 26, 28 described herein. Arms 526, 528 each extend parallel to axis DD. Arms 526, 528 each include an arcuate outer surface extending between a pair of side surfaces. At least one of the outer surfaces and the side surfaces of arms 526, 528 have at least one recess or cavity 530, 532 therein, configured to receive an insertion tool, compression instrument and/or instruments for inserting and tensioning bone fastener 512.

Arm 526 includes a proximal end 534 configured for connection with an extension 536, similar to extension 36. Arm 528 includes a proximal end 538 configured for connection with an extension 540, similar to extension 40. Extensions 536, 540 each include an arcuate outer surface extending between a pair of side surfaces. At least one of the outer surfaces and the side surfaces of extensions 536, 540 have at least one recess or cavity 539, 541 therein, configured to receive an insertion tool, compression instrument and/or instruments for inserting and tensioning bone fastener 512.

Receiver 520 includes an implant receiving surface 542, similar to implant receiving surface 42 described herein. Implant receiving surface 542 is configured for engagement with surfaces of spinal rod 14. Implant receiving surface 542 includes a saddle 570, similar to saddle 70 described herein. Proximal ends 534, 538 and implant receiving surface 542 define an implant cavity 544, similar to cavity 44 described herein.

Arm 526 is connected to extension 536 via a break away surface 546, similar to break away surface 46 described herein. Arm 528 is connected to extension 540 via a break away surface 548, similar to break away surface 48 described herein. Break away surfaces 546, 548 are configured to fracture and separate at a predetermined force or torque limit, described herein. Break away surfaces 546, 548 are configured to fracture and separate from receiver 520 to enable a minimally invasive surgical procedure, described herein. Break away surfaces 546, 548 are configured to control the location and consistency of the resulting fracture surface thereby minimizing the negative impact to soft tissue surrounding bone fastener 512.

Arm 526 defines a proximal shoulder 550 including proximal most end surface 534, and arm 528 defines a proximal shoulder 552 including proximal most end surface 538. Break away surface 546 includes an undercut 554 being recessed within proximal shoulder 550, and break away surface 548 includes an undercut 556 being recessed within proximal shoulder 552. Undercuts 554, 556 are configured to form a shroud about a perimeter of shoulders 550, 552 when extensions 536, 540 fracture and separate from receiver 520, thereby reducing potential contact and/or injury to soft tissue surrounding bone fastener 512.

Break away surface 546 includes a circumferential wall 558, similar to wall 58 described herein, configured to connect arm 526 to extension 536, and break away surface 548 includes a circumferential wall 560, similar to wall 60 described herein, configured to connect arm 528 to extension 540.

Proximal most end surfaces 534, 538 define a proximal boundary 562 of cavity 544 and implant receiving surface 542 defines a distal boundary 564 of cavity 544. Receiver 520 includes inner threaded surfaces 566, 568 extending along at least a portion of arms 526, 528 and extensions 536, 540. Inner threaded surfaces 566, 568 are configured for engagement with a set screw (not shown).

Implant receiving surface 542 includes saddle 570 configured to receive spinal rod 14. Saddle 570 includes an end 572 and an end 574. End 572 is configured to receive spinal rod 14 and end 574 is configured for engagement with a head 502 of a shaft 500 of bone fastener 512.

Receiver 520 includes an inner surface that defines a circumferential upper groove 576 configured for disposal of a resilient member, for example, a ring 578, as shown in FIG. 30. Ring 578 is contractable in upper groove 576. Ring 578 includes a circumference that defines an opening, for example, a gap. In some embodiments, the gap is sized such that the gap has a thickness that is less than the height and the width. In some embodiments, the gap is sized to allow ring 578 to translate through cavity 544 by contracting circumferentially. In some embodiments, upon disposal of ring 578 with upper groove 576, surfaces of upper groove 576 resist and/or prevent axial translation of ring 578 relative to axis DD.

Receiver 520 includes an inner surface that defines a circumferential lower groove 580. Lower groove 580 is configured for disposal of a resilient member, for example, a ring 582. Ring 582 is expandable in lower groove 580 to connect receiver 520 and shaft 500. Ring 582 includes a circumference that defines an opening, for example, a gap. In some embodiments, the gap is sized such that the gap has a thickness that is less than the height and the width. In some embodiments, the gap is sized to allow ring 582 to translate through cavity 544 by contracting circumferentially. In some embodiments, upon disposal of ring 582 with lower groove 580, surfaces of lower groove 580 resist and/or prevent axial translation of ring 582 relative to axis DD. The inner surface defines an expansion groove 584.

Rings 578, 582 facilitate manual engagement/connection of receiver 520 and shaft 500. In some embodiments, rings 578, 582 facilitate manual engagement/connection of receiver 520 and shaft 500 such that shaft 500 is attached with receiver 520 in a non-instrumented snap-fit assembly, as described herein. In some embodiments, receiver 520 is configured for a pop-on engagement with shaft 500.

In some embodiments, manual engagement and/or non-instrumented assembly includes a practitioner, surgeon and/or medical staff grasping shaft 500 and receiver 520 and forcibly snap fitting the components together, as described herein. In some embodiments, manual engagement and/or non-instrumented assembly includes a practitioner, surgeon and/or medical staff grasping shaft 500 and receiver 520 and forcibly pop fitting the components together and/or pop fitting receiver 520 onto shaft 500, as described herein. In some embodiments, a force in a range of 2-50 N is required to manually engage shaft 500 and receiver 520 and forcibly assemble the components. For example, a force in a range of 2-50 N is required to snap fit and/or pop fit assemble shaft 500 and receiver 520. In some embodiments, a force in a range of 5-10 N is required to manually engage shaft 500 and receiver 520 and forcibly assemble the components. For example, a force in a range of 5-10 N is required to snap fit and/or pop fit assemble shaft 500 and receiver 520. In some embodiments, shaft 500 is manually engaged with receiver 520 in a non-instrumented assembly, as described herein, such that removal of receiver 520 and shaft 500 requires a force and/or a pull-out strength of at least 5000 N. In some embodiments, this configuration provides manually engageable components that are assembled without instrumentation, and subsequent to assembly, the assembled components have a selected pull-out strength and/or can be pulled apart, removed and/or separated with a minimum required force.

In one embodiment, spinal implant system 10, similar to the systems and methods described herein, is employed for minimally invasively surgically implementing a navigation technique for posterior cervical spinal fixation, as shown in FIGS. 31-56. For example, spinal implant system 10 can include cervical pedicle screws that provide biomechanical fixation. In some embodiments, spinal implant system 10, is employed with a minimally invasive, navigated cervical pedicle screw fixation technique that provides a biomechanical construct and can also be applied to percutaneous, navigated C1 lateral mass-C2 pars/pedicle screw/rod fixation and C1-2 trans articular screw fixation.

In some embodiments, spinal implant system 10 combines intraoperative navigation and minimally invasive muscle-splitting techniques. In some embodiments, spinal implant system 10 includes a minimally invasive muscle-sparing technique that allows for a biomechanically lateral to medial trajectory with a larger diameter and longer screws while minimizing soft tissue exposure morbidity.

In some embodiments, spinal implant system 10 includes a navigated percutaneous, minimally invasive cervical pedicle screw fixation technique that achieves fixation. In some embodiments, the technique is a safer, less invasive method for fixating the atlanto-axial (C1-2) and subaxial cervico-thoracic spine (C3-T2).

Figure 31:
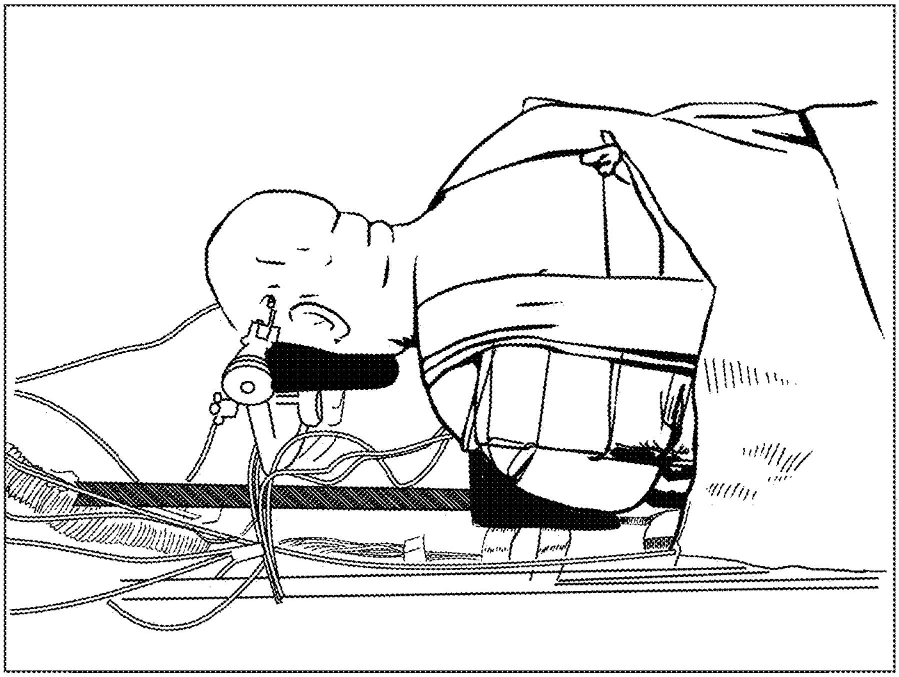
FIG. 31 is a perspective view of components of one embodiment of a spinal implant system in accordance with the principles of the present disclosure disposed with an anatomy.

For example, the technique employs spinal implant system 10 and includes placing the patient in a frame and positioning the patient in a prone position on a table with an attachment or cervical management system, as shown in FIG. 31. Alignment of cervicothoracic junction is maintained in a neutral position if fixating across the cervicothoracic junction. The head of the patient is maintained in a neutral position during positioning. In some embodiments, in C1-2 fixation, a slightly flexed position provides better access to the C1 lateral masses, and is re-positioned appropriately once screws have been placed prior to rod placement. Taping the shoulders down allows for access to the lateral neck.

Figure 32:
FIG. 32 is a perspective view of components of one embodiment of a spinal implant system in accordance with the principles of the present disclosure disposed with an anatomy.

Sterile preparation is performed, as shown in FIG. 32. Sterile preparation is prepared wide on the neck due to the lateral to medial angle for percutaneous pedicle screw placement.

Intra-operative imaging is obtained, either cone-beam CT or 2-D fluoroscopy, for use with an intra-operative navigation system, as shown in FIG. 32. In some embodiments, in sub-axial fixation (C3-T2), a fiducial is placed on a spinous process caudal to the lowest instrumented vertebra. In some embodiments, in atlanto-axial fixation, an array fiducial attachment is placed directly on the retractor or on the C2 spinous process.

Figure 33:
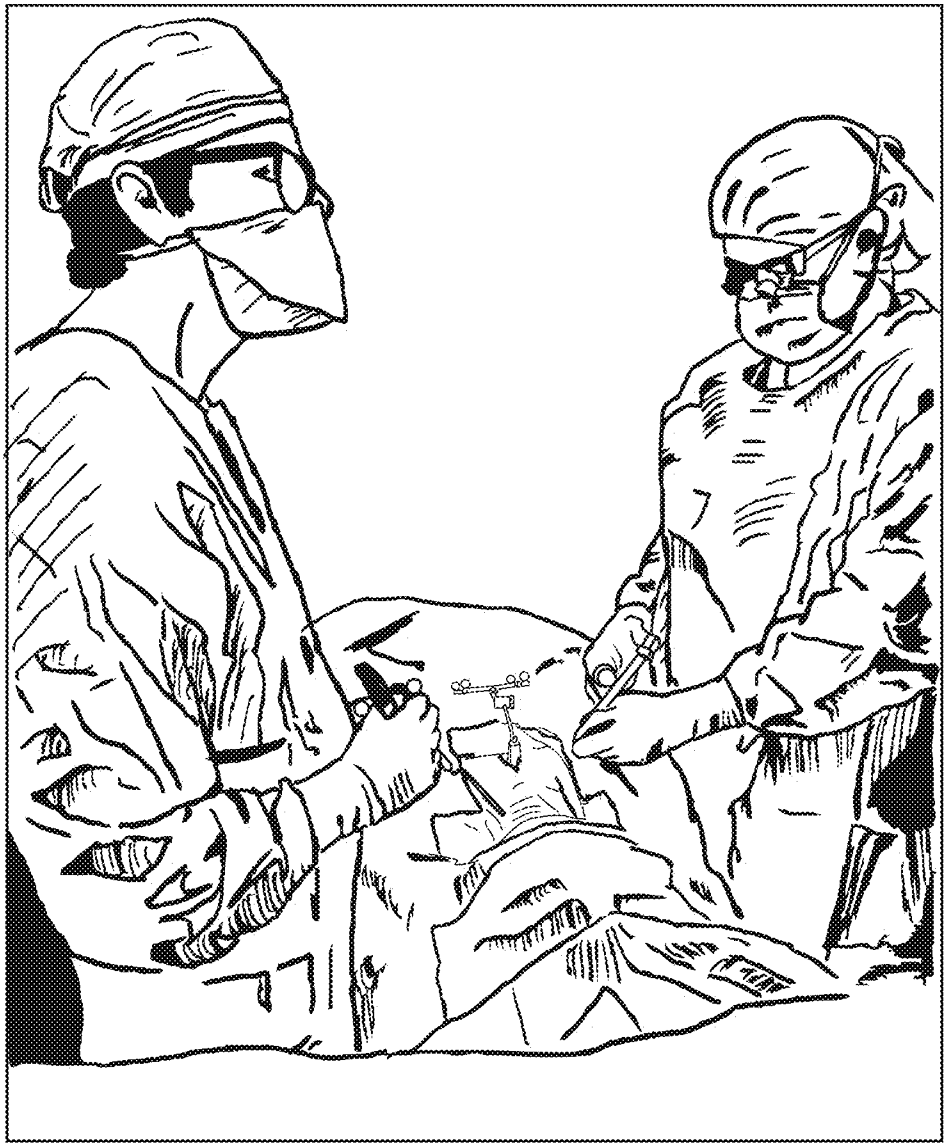
FIG. 33 is a perspective view of components of one embodiment of a spinal implant system in accordance with the principles of the present disclosure disposed with an anatomy.

The percutaneous incision is planned once the fiducial arrays have been placed and an intra-operative CT is performed, as shown in FIG. 33. In some embodiments, a navigated wand with an extended projection is used to demonstrate the necessary entry point to provide the desired trajectory.

Figure 34:
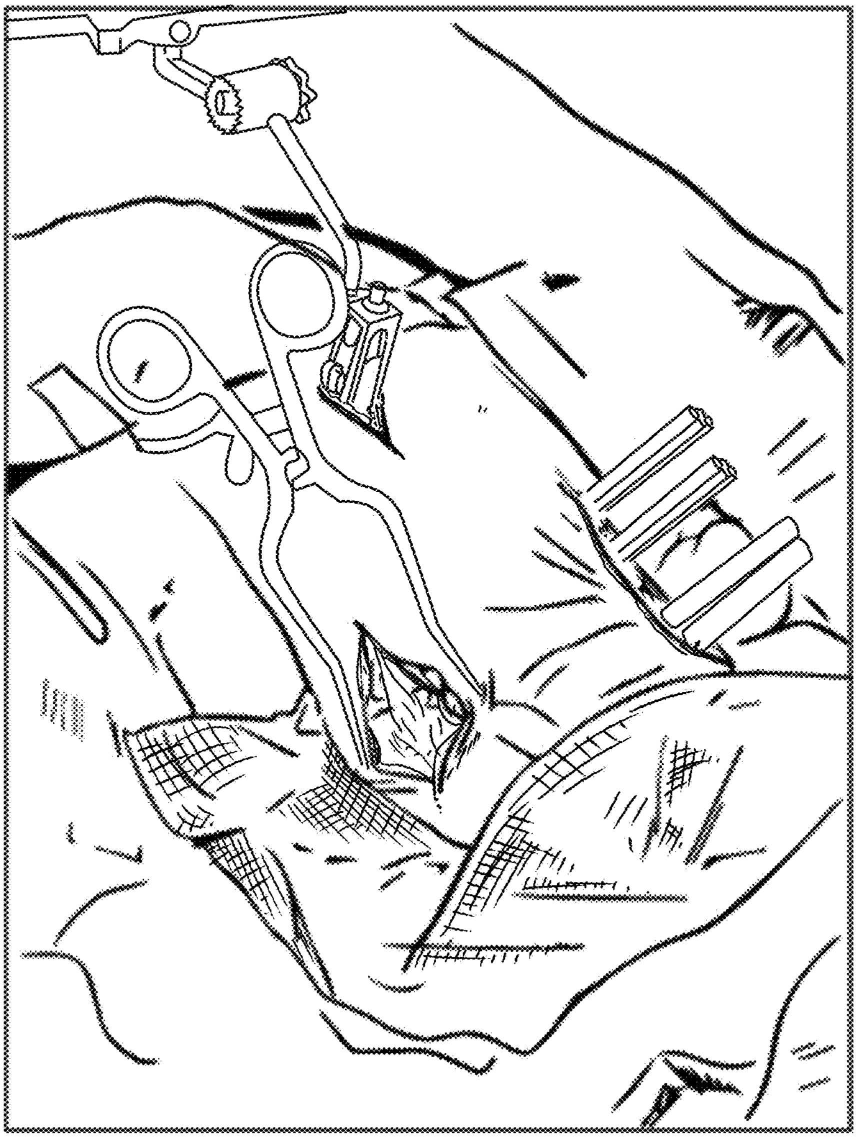
FIG. 34 is a perspective view of components of one embodiment of a spinal implant system in accordance with the principles of the present disclosure disposed with an anatomy.

A linear incision is made through the dermis down to the level of investing fascia along the course of the entry points once each entry point is identified, as shown in FIG. 34. In some embodiments, the incision provides a cosmetic closure as opposed to several small stab incisions which can alternatively be employed. In some embodiments, a small self-retaining retractor is utilized.

Figure 35:
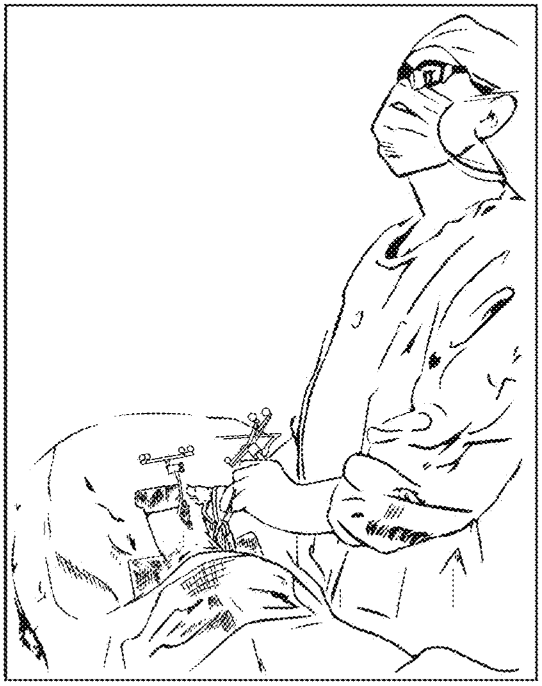
FIG. 35 is a perspective view of components of one embodiment of a spinal implant system in accordance with the principles of the present disclosure disposed with an anatomy.

The percutaneous entry point is determined through the fascia via a navigated wand. Electrocautery is used down through the fascia, and the muscle fibers are split bluntly in the cephalad-caudal plane. Any deep fascia layers can be released with the electrocautery to allow for placement of the navigated drill onto the lateral mass (alternatively a 2 mm burr can be utilized). In some embodiments, electrocautery may be navigated to remove soft tissue from the pilot hole screw entry site. The drill is used to make a pilot hole, as shown in FIG. 35. The pilot hole accepts the drilling and tapping portions of the procedure with or without direct visualization. Trajectory is confirmed with the navigated drill corresponding to the diameter of the desired screw and drill is advanced into the lateral mass along the axis of the pedicle.

Figure 36:
FIG. 36 is a perspective view of components of one embodiment of a spinal implant system in accordance with the principles of the present disclosure disposed with an anatomy.

The drill is advanced at least mid-way through the pedicle. A 3.0 mm navigated tap is then used and advanced into the vertebral body, as shown in FIG. 36. In instances of small pedicle size, the pedicle itself may not be fully cannulated with the drill and/or the tap. Screw placement may proceed along the trajectory of the pedicle, however, may stop short of traversing the pedicle. The navigated drill and tap is undersized and tapered to enter the pilot hole and advance without the need for direct visualization.

Figure 37:
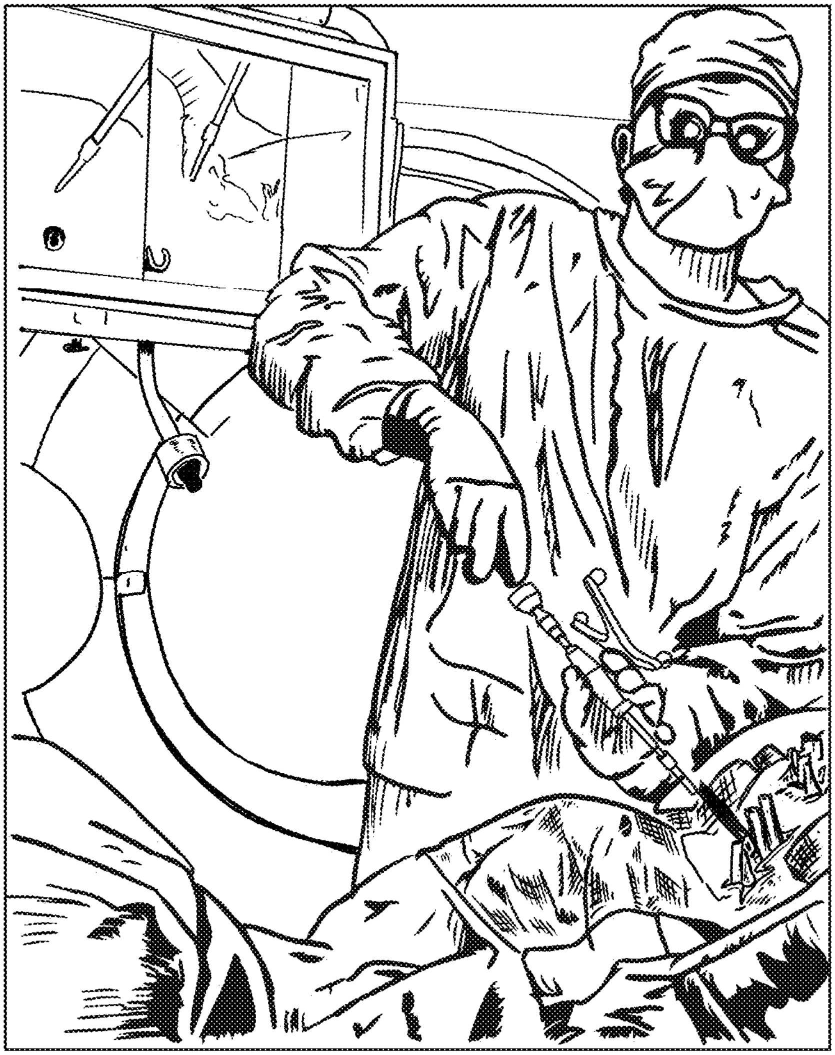
FIG. 37 is a perspective view of components of one embodiment of a spinal implant system in accordance with the principles of the present disclosure disposed with an anatomy.
Figure 38:
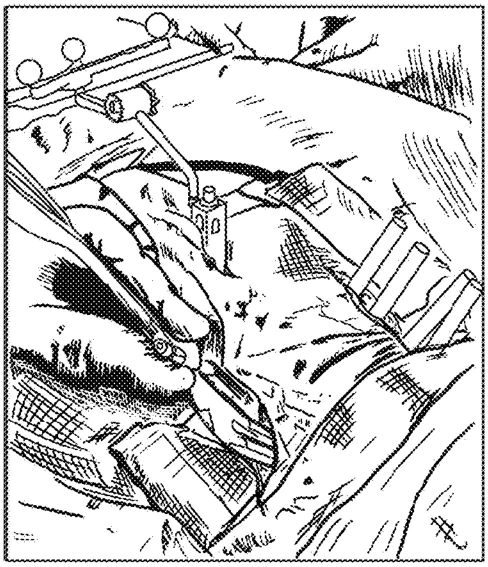
FIG. 38 is a perspective view of components of one embodiment of a spinal implant system in accordance with the principles of the present disclosure disposed with an anatomy.
Figure 39:
FIG. 39 is a perspective view of components of one embodiment of a spinal implant system in accordance with the principles of the present disclosure disposed with an anatomy.
Figure 40:
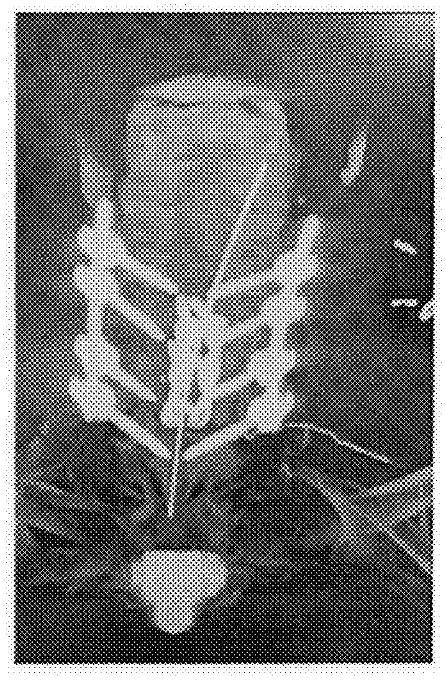
FIG. 40 is an image of components of one embodiment of a spinal implant system in accordance with the principles of the present disclosure disposed with vertebrae.
Figure 41:
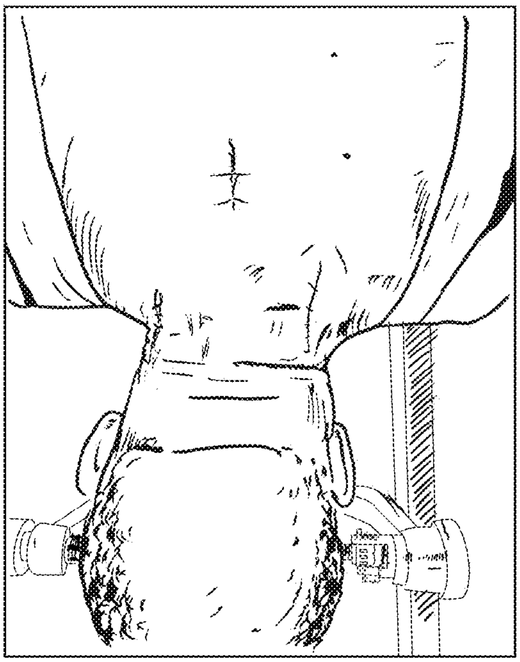
FIG. 41 is a top view of components of one embodiment of a spinal implant system in accordance with the principles of the present disclosure disposed with an anatomy.

The tap is projected on and an appropriately sized screw is measured using the navigation system, as shown in FIG. 37. A navigated screwdriver with a screw and an extender, for example, a reduction tower is then placed under navigation. A spinal rod is translated through the reduction towers after placement of pedicle screws on both sides, as shown in FIG. 38. The rod is translated using a percutaneous technique and tested to confirm to be through all reduction towers. Locking caps are placed and finally tightened, as shown in FIG. 39. The rod holder is removed and final imaging is performed, as shown in 40. The muscle, fascia and skin are closed in layers, as shown in FIG. 41. In some embodiments, the present technique does not employ reduction towers, for example, for a C1 lateral mass-C2 pars/pedicle fixation or C1-2 trans articular screw fixation. In some embodiments, the present technique can be used to place percutaneous lateral mass fixation by angling the screw in a medial to lateral trajectory in the plane of the lateral mass.

Figure 42:
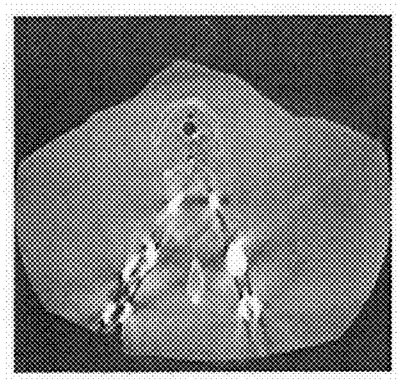
FIG. 42 is an image of components of one embodiment of a spinal implant system in accordance with the principles of the present disclosure disposed with vertebrae.
Figure 43:
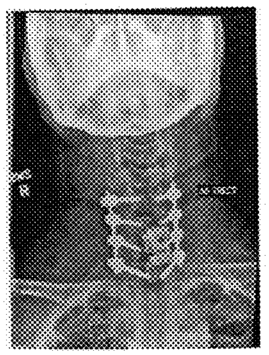
FIG. 43 is an image of components of one embodiment of a spinal implant system in accordance with the principles of the present disclosure disposed with vertebrae.
Figure 44:
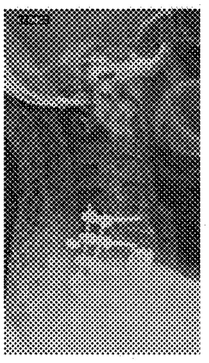
FIG. 44 is an image of components of one embodiment of a spinal implant system in accordance with the principles of the present disclosure disposed with vertebrae.
Figure 45:
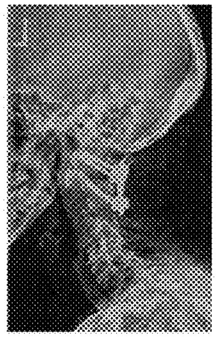
FIG. 45 is an image of components of one embodiment of a spinal implant system in accordance with the principles of the present disclosure disposed with vertebrae.
Figure 46:
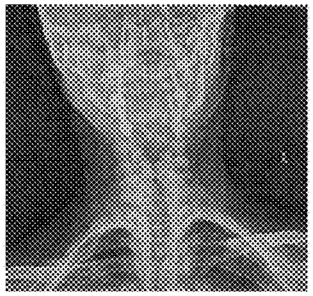
FIG. 46 is an image of components of one embodiment of a spinal implant system in accordance with the principles of the present disclosure disposed with vertebrae.
Figure 47:
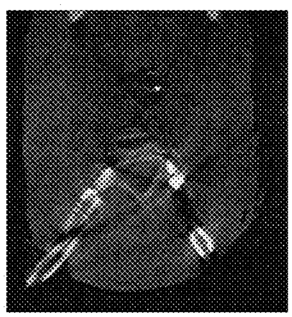
FIG. 47 is an image of components of one embodiment of a spinal implant system in accordance with the principles of the present disclosure disposed with vertebrae.
Figure 48:
FIG. 48 is an image of components of one embodiment of a spinal implant system in accordance with the principles of the present disclosure disposed with vertebrae.
Figure 49:
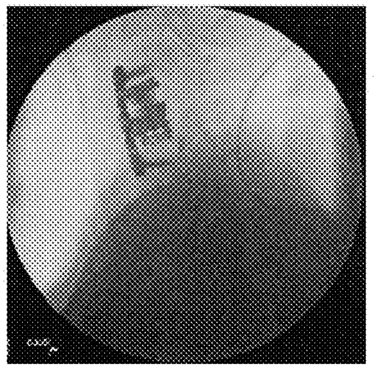
FIG. 49 is an image of components of one embodiment of a spinal implant system in accordance with the principles of the present disclosure disposed with vertebrae.
Figure 50:
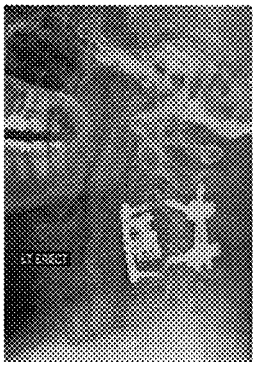
FIG. 50 is an image of components of one embodiment of a spinal implant system in accordance with the principles of the present disclosure disposed with vertebrae.
Figure 51:
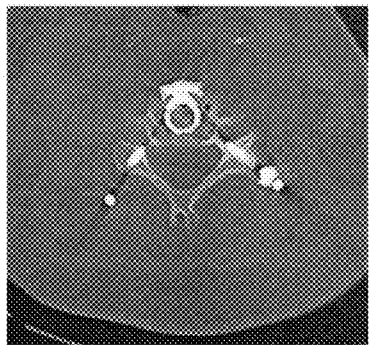
FIG. 51 is an image of components of one embodiment of a spinal implant system in accordance with the principles of the present disclosure disposed with vertebrae.
Figure 52:
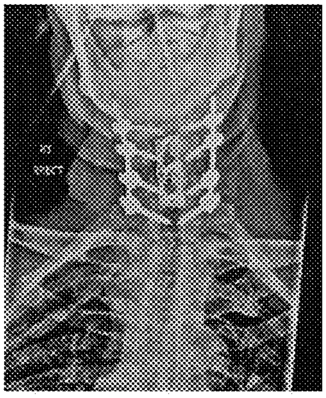
FIG. 52 is an image of components of one embodiment of a spinal implant system in accordance with the principles of the present disclosure disposed with vertebrae.
Figure 53:
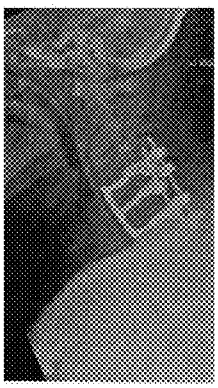
FIG. 53 is an image of components of one embodiment of a spinal implant system in accordance with the principles of the present disclosure disposed with vertebrae.
Figure 54:
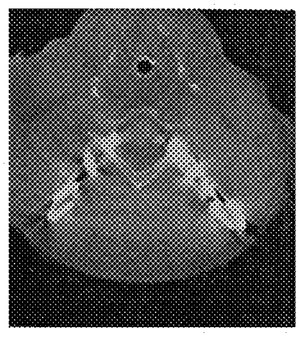
FIG. 54 is an image of components of one embodiment of a spinal implant system in accordance with the principles of the present disclosure disposed with vertebrae.
Figure 55:
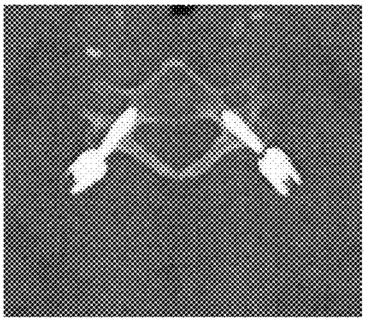
FIG. 55 is an image of components of one embodiment of a spinal implant system in accordance with the principles of the present disclosure disposed with vertebrae.
Figure 56:
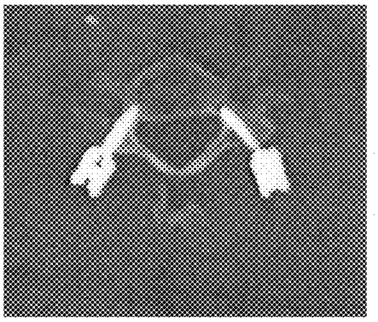
FIG. 56 is an image of components of one embodiment of a spinal implant system in accordance with the principles of the present disclosure disposed with vertebrae.

Intraoperative and postoperative imaging shows C5-T1 construct. FIG. 42 is an axial CT at the C5 pedicle. FIGS. 43-44 show postoperative plain radiographs, anteroposterior (FIG. 43) and lateral (FIG. 44) of the final construct. FIGS. 45-46 show post-operative plain radiographs anteroposterior (FIG. 46) and lateral (FIG. 45) of a C1-2 construct. FIG. 47 shows an axial intra-operative CT image with screws entering the pedicles bilaterally. Imaging of a postoperative anterior and posterior construct at C4-5 is shown in FIG. 48. Imaging of C4 corpectomy with anterior plating is shown in FIG. 49. Imaging of posterior instrumentation at C3-05 is shown in FIG. 50. Imaging of narrow pedicles that limit length of screws placed is shown in FIG. 51. Post-operative AP imaging with C5-T1 percutaneous pedicle screw fixation is shown in FIG. 52. Post-operative lateral imaging with C5-T1 percutaneous pedicle screw fixation is shown in FIG. 53. Intraoperative CT C spine imaging with C5 pedicle screws is shown in FIG. 54. Postoperative CT imaging demonstrating bilateral C5 pedicle screws is shown in FIG. 55. Postoperative CT imaging demonstrating bilateral C6 pedicle screws is shown in FIG. 56.

In some embodiments, spinal implant system 10, similar to the systems and methods described herein, is employed for minimally invasively surgically implementing a navigation technique for posterior cervical spinal fixation. The technique includes positioning the patient in a prone position; preparing the patient and draping widely; performing intra-operative imaging for use with intra-operative navigation; placing a navigation fiducial array; planning incision and screw placement; drilling a screw entry point to accommodate drilling and tapping without direct visualization; drilling pedicle/bone and tapping under intra-operative navigated guidance; placing screws under intra-operative navigated guidance; passing a percutaneous rod through reduction towers and applying locking caps; and closing the wound.

In some embodiments, spinal implant system 10, similar to the systems and methods described herein, is employed for minimally invasively surgically implementing a navigated percutaneous pedicle screw fixation technique. In some embodiments, the technique circumvents the drawbacks of open pedicle screw fixation including blood loss, muscle morbidity and pain associated with the posterior cervical approach. In some embodiments, the technique facilitates accurate, navigated, minimally invasive, muscle-splitting screw placement with biomechanical fixation. In some embodiments, the technique obviates the need for intra-operative fluoroscopy or specialized tubular/cylindrical retractors. In some embodiments, the technique includes positioning the patient in a prone position and the patient is prepped widely to allow for a lateral to medial, muscle-sparing approach. In some embodiments, intra-operative navigation is accomplished by placing a navigation fiducial on the headframe or C2 spinous process for C1-2 fixation and on an upper thoracic spinous process for C3-T2 screw/rod fixation. In some embodiments, intra-operative flat panel or cone beam computed tomography CT, 2-D or 3-D fluoroscopy is utilized to obtain imaging for use with intra-operative spinal navigation. In some embodiments, navigation is utilized to plan and execute bilateral skin incisions over the bony anatomy, for example, the pedicle to be fixated. In some embodiments, sharp and blunt dissection is accomplished to expose the screw entry point typically on the lateral mass. In some embodiments, a screw entry point is drilled with a navigated high-speed drill using a small burr or drill without the need for direct visualization. In some embodiments, screw lateral to medial trajectory is drilled and tapped under navigated guidance. In some embodiments, the screw is placed under navigated guidance. In some embodiments, the rod is then passed percutaneously through extender tabs attached to the screws from C3-T2 or under direct visualization at C1-2. In some embodiments, locking screws are applied and the wound is closed.

In some embodiments, spinal implant system 10, similar to the systems and methods described herein, is employed for minimally invasively surgically implementing a navigated percutaneous pedicle screw fixation technique. In some embodiments, the technique includes positioning the patient prone and prepping widely to allow for a lateral to medial, muscle-sparing approach. Intra-operative navigation is accomplished by placing a navigation fiducial on the headframe or on the C2 spinous process for C1-2 fixation and on an upper thoracic spinous process for C3-T2 screw/rod fixation. Intra-operative flat panel or cone beam computed tomography CT, 2-D or 3-D fluoroscopy is utilized to obtain imaging for use with intra-operative spinal navigation. Navigation is utilized to plan and execute bilateral lateral skin incisions over the bony anatomy, for example, pedicle to be fixated. Sharp and blunt dissection is accomplished to expose screw entry point typically on the lateral mass. A screw entry point is drilled with a navigated high-speed drill using a small burr or drill. The soft tissue and fascia around the lateral masses can provide difficulty with cannulating the initial pilot hole and tapped trajectory. In some embodiments, to prevent this from occurring, an appropriate corridor is confirmed through the lateral neck musculature and fascia. If there is any resistance encountered with cannulating the entry point or obtaining screw purchase, re-orientation with the navigated wand and widening any muscle and fascia near the lateral mass entry point is performed. The pilot holes provide entrance of the drill and tap without direct visualization. Screw lateral to medial trajectory is drilled and tapped under navigated guidance. The screw is placed under navigated guidance. The rod is passed percutaneously through extender tabs attached to the screws from C3-T2 or under direct visualization at C1-2. In some embodiments, to reduce the risk of bilateral vertebral artery injury, screws are placed on one side at a time. In some embodiments, if there is any concern for significant breach or inaccuracy of the navigation, an intraoperative CT is performed prior to proceeding with the contralateral side to confirm that there has not been significant foraminal breach and potential vertebral artery compromise. Locking screws are applied and the wound is closed.

In some embodiments, the minimally invasive, navigated posterior cervical screw/rod fixation technique utilizes intra-operative navigation which includes robot-assisted intra-operative navigation to improve the technique. This also includes augmented reality navigation to improve the technique.

In some embodiments, the technique can be utilized with or without the need for a tubular/cylindrical retractor. In some embodiments, the technique can be utilized with or without extender tab screws. In some embodiments, the technique can be utilized for stand-alone posterior cervical fixation. In some embodiments, the technique can be utilized in conjunction with minimally invasive or open posterior cervical decompression. In some embodiments, the technique can be used in conjunction with anterior cervical decompression and stabilization as part of a posterior-anterior or anterior-posterior single or staged surgical procedure.

In some embodiments, spinal implant system 10, similar to the systems and methods described herein, is employed for minimally invasively surgically implementing a navigated percutaneous pedicle screw fixation technique. In some embodiments, the technique includes positioning the patient in a head fixation, prone on the operating room table. The patient is prepped and draped widely to facilitate a bilateral, lateral to medial approach. Intra-operative navigation fiducials are placed on the head frame or in the C2 spinous process for posterior C1-2 screw/rod fixation or on a lower cervical or an upper thoracic spinous process for sub axial C3-T2 fixation. Intra-operative cone-beam CT or fluoroscopic images are obtained for use with intra-operative navigation. Using navigation, lateral skin incision(s) are planned parallel to the targeted cervical pedicles. A lateral to medial soft tissue, muscle-splitting corridor is dissected. Using navigation, a screw entry point is drilled in the targeted lateral mass parallel to the pedicle. The targeted pedicle is drilled, tapped and the screw is placed under navigated guidance. After all targeted screws are placed bilaterally, percutaneous rods are passed bilaterally through the extender tabs and locking caps are engaged. The wounds are closed. In some embodiments, the technique employs robotic/robot-assisted or augmented reality intra-operative navigation, described herein.

In some embodiments, spinal implant system 10, similar to the systems and methods described herein, is employed in a method for treating a spine, which includes the steps of imaging a patient anatomy including a surgical site; selecting a minimally invasive pathway including a pedicle of at least one cervical vertebra of the patient anatomy; creating a cavity in at least a portion of the pedicle with at least one surgical instrument including a surgical navigation component generating a signal representative of a position of the surgical instrument relative to the surgical site; and engaging a bone screw, for example, bone fastener 12/bone fastener 212, with the at least a portion of the pedicle with a surgical driver including a surgical navigation component generating a signal representative of a position of the surgical driver and/or bone screw relative to the surgical site.

In some embodiments, the step of selecting the pathway includes a substantially lateral to medial trajectory of the patient anatomy. In some embodiments, the step of selecting the pathway includes a lateral mass of a first cervical vertebra, and a pedicle or pars interarticularis of a second cervical vertebra. In some embodiments, the step of selecting the pathway includes a medial trajectory along the trajectory of the lateral mass.

In some embodiments, the step of engaging includes a trans articular fixation of the first cervical vertebra and the second cervical vertebra. In some embodiments, the step of engaging includes a fixation of a first cervical vertebra and a first thoracic vertebra. In some embodiments, the method further comprises the step of engaging a minimally invasive spinal rod, for example, spinal rod 14 with the bone screw.

In some embodiments, the at least one surgical instrument includes a surgical drill including a surgical navigation component and a surgical tap including a surgical navigation component. In some embodiments, the bone screw, for example, bone fastener 12 includes a receiver, for example, receiver 20 including a first arm, for example, arm 26 connected to a first extension, for example, extension 36 and a second arm, for example, arm 28 connected to a second extension, for example, extension 40, the arms being connected to the extensions via a break away surface, for example, break away surfaces 46, 48, the arms including a proximal most end surface, for example, proximal most end surfaces 34, 38 and the receiver further including an implant receiving surface, for example, implant receiving surface 42, the proximal most end surface and the implant receiving surface defining an implant cavity, for example, cavity 44, the break away surface being disposed within the implant cavity, and a threaded shaft, for example, shaft 100 connectable with the receiver and engageable with the at least a portion of the pedicle. In some embodiments, the receiver defines a longitudinal axis and the proximal most end surface defines a transverse plane, the break away surface being axially spaced from the transverse plane.

In some embodiments, the step of creating a cavity includes disposing a guide member with the patient anatomy, the guide member being configured for disposal of the at least one surgical instrument and an image guide being oriented relative to a sensor to communicate a signal representative of a position of the guide member, the guide member including an end effector of a robotic arm. In some embodiments, a tracking device is provided that includes a sensor that receives the signal and communicates with a processor to generate data for display of an image from a monitor, the image representing position of the guide member relative to the surgical site.

In some embodiments, a method for treating a spine is provided. In some embodiments, the method comprises the steps of imaging a patient anatomy including a surgical site; selecting a minimally invasive pathway of the patient anatomy including a lateral mass of a first cervical vertebra and a pedicle of a second cervical vertebra; creating a cavity in at least a portion of the pedicle and at least a portion of the lateral mass with at least one surgical instrument including a surgical navigation component generating a signal representative of a position of the surgical instrument relative to the surgical site; engaging a bone screw, for example, bone fastener 12/bone fastener 212 with the at least a portion of the pedicle and the at least a portion of the lateral mass, with a surgical driver including a surgical navigation component generating a signal representative of a position of the surgical driver and/or bone screw relative to the surgical site, the bone screw being engaged with the at least a portion of the pedicle and the at least a portion of the lateral mass for trans articular fixation of the first cervical vertebra and the second cervical vertebra; and engaging a minimally invasive spinal rod with the bone screw.

In some embodiments, the at least one surgical instrument includes a surgical drill including a surgical navigation component and a surgical tap including a surgical navigation component.

In some embodiments the bone screw, for example, bone fastener 12 includes a receiver, for example, receiver 20, including a first arm, for example, arm 26 connected to a first extension, for example, extension 36, and a second arm, for example, arm 28, connected to a second extension, for example extension 40, the arms being connected to the extensions via a break away surface, for example break away surfaces 46, 48, the arms including a proximal most end surface, for example, proximal most end surfaces 34, 38, and the receiver further including an implant receiving surface, for example, implant receiving surface 42, the proximal most end surface and the implant receiving surface defining an implant cavity, for example, cavity 44, the break away surface being disposed within the implant cavity, and a threaded shaft, for example, shaft 100, connectable with the receiver and engageable with the at least a portion of the pedicle and the at least a portion of the lateral mass. In some embodiments, the receiver defines a longitudinal axis and the proximal most end surface defines a transverse plane, the break away surface being axially spaced from the transverse plane.

In some embodiments, the step of creating a cavity includes disposing a guide member with the patient anatomy, the guide member being configured for disposal of the at least one surgical instrument and an image guide being oriented relative to a sensor to communicate a signal representative of a position of the guide member, the guide member including an end effector of a robotic arm. In some embodiments, a tracking device is provided that includes a sensor that receives the signal and communicates with a processor to generate data for display of an image from a monitor, the image representing position of the guide member relative to the surgical site.

In some embodiments, a method for treating a spine, the method comprising the step of imaging a patient anatomy including a surgical site; selecting a minimally invasive pathway including a pedicle of at least one cervical vertebra of the patient anatomy; creating a cavity in at least a portion of the pedicle with at least one surgical instrument including a surgical navigation component generating a signal representative of a position of the surgical instrument relative to the surgical site; and engaging a bone screw, for example, bone fastener 12/bone fastener 212, with the at least a portion of the pedicle with a surgical driver including a surgical navigation component generating a signal representative of a position of the surgical driver and/or bone screw relative to the surgical site, the bone screw including a receiver, for example, receiver 20, including a first arm, for example, arm 26, connected to a first extension, for example, extension 36, and a second arm, for example, arm 28, connected to a second extension, for example, extension 40, the arms being connected to the extensions via a break away surface, for example, break away surfaces 46, 48, the arms including a proximal most end surface, for example, proximal most end surfaces 34, 38, and the receiver further including an implant receiving surface, for example, implant receiving surface 42, the proximal most end surface and the implant receiving surface defining an implant cavity, for example, cavity 44, the break away surface being disposed within the implant cavity, and a threaded shaft, for example, shaft 100, connectable with the receiver and engageable with the at least a portion of the pedicle.

In some embodiments, the receiver defines a longitudinal axis and the proximal most end surface defines a transverse plane, the break away surface being axially spaced from the transverse plane. In some embodiments, the step of selecting the pathway includes a lateral mass of a first cervical vertebra, and a pedicle of a second cervical vertebra.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method for treating a spine, the method comprising the steps of:

imaging a patient anatomy including a surgical site;

selecting a minimally invasive pathway including a pedicle of a first cervical vertebra and a lateral mass of a second cervical vertebra;

creating a cavity in the pedicle with at least one surgical instrument including a surgical navigation component generating a signal representative of a position of the surgical instrument relative to the surgical site; and engaging a bone screw with the pedicle with a surgical driver including a surgical navigation component generating a signal representative of a position of the surgical driver and/or the bone screw relative to the surgical site.

2. A method as recited in claim 1, wherein the step of selecting the pathway includes a substantially lateral to medial trajectory of the patient anatomy.

3. A method as recited in claim 1, wherein the step of engaging includes a trans articular fixation of the first cervical vertebra and the second cervical vertebra.

4. A method as recited in claim 1, further comprising the step of engaging a minimally invasive spinal rod with the bone screw.

5. A method as recited in claim 1, wherein the at least one surgical instrument includes a surgical drill including a surgical navigation component and a surgical tap including a surgical navigation component.

6. A method as recited in claim 1, wherein the bone screw includes:

a receiver including a first arm connected to a first extension and a second arm connected to a second extension, the arms being connected to the extensions via a break away surface, the arms including a proximal shoulder disposed about the break away surface and the receiver further including an implant receiving surface, the proximal shoulder and the implant receiving surface defining an implant cavity, and a threaded shaft connectable with the receiver and engageable with the pedicle.

7. A method as recited in claim 6, wherein the receiver defines a longitudinal axis and the proximal shoulder defines a transverse plane, the break away surface being axially spaced from the transverse plane.

8. A method as recited in claim 1, wherein the bone screw includes:

a receiver having an inner threaded surface and including a first arm connected to a first extension and a second arm connected to a second extension, the arms being connected to the extensions via a break away surface defining a shear ring including a helical configuration disposed in helical alignment with the inner threaded surface.

9. A method as recited in claim 1, wherein the step of creating a cavity includes disposing a guide member with the patient anatomy, the guide member being configured for disposal of the at least one surgical instrument and an image guide being oriented relative to a sensor to communicate a signal representative of a position of the guide member, the guide member including an end effector of a robotic arm.

10. A spinal implant system as recited in claim 9, further comprising a tracking device including a sensor that receives the signal and communicates with a processor to generate data for display of an image from a monitor, the image representing position of the guide member relative to the surgical site.

11. A method for treating a spine, the method comprising the steps of:

imaging a patient anatomy including a surgical site;

selecting a minimally invasive pathway of the patient anatomy including a pedicle of a first cervical vertebra and a lateral mass of a second cervical vertebra;

creating a cavity in the pedicle and the lateral mass with at least one surgical instrument including a surgical navigation component generating a signal representative of a position of the surgical instrument relative to the surgical site;

engaging a bone screw with the pedicle and the lateral mass, with a surgical driver including a surgical navigation component generating a signal representative of a position of the surgical driver and/or bone screw relative to the surgical site, the bone screw being engaged with the pedicle and the lateral mass for trans articular fixation of the first cervical vertebra and the second cervical vertebra; and engaging a minimally invasive spinal rod with the bone screw.

12. A method as recited in claim 11, wherein the at least one surgical instrument includes a surgical drill including a surgical navigation component and a surgical tap including a surgical navigation component.

13. A method as recited in claim 11, wherein the bone screw includes:

a receiver including a first arm connected to a first extension and a second arm connected to a second extension, the arms being connected to the extensions via a break away surface, the arms including a proximal shoulder disposed about the break away surface and the receiver further including an implant receiving surface, the proximal shoulder and the implant receiving surface defining an implant cavity, and a threaded shaft connectable with the receiver and engageable with the at least a portion of the pedicle.

14. A method as recited in claim 13, wherein the receiver defines a longitudinal axis and the proximal shoulder defines a transverse plane, the break away surface being axially spaced from the transverse plane.

15. A method as recited in claim 13, wherein the step of creating a cavity includes disposing a guide member with the patient anatomy, the guide member being configured for disposal of the at least one surgical instrument and an image guide being oriented relative to a sensor to communicate a signal representative of a position of the guide member, the guide member including an end effector of a robotic arm.

16. A spinal implant system as recited in claim 15, further comprising a tracking device including a sensor that receives the signal and communicates with a processor to generate data for display of an image from a monitor, the image representing position of the guide member relative to the surgical site.

17. A method for treating a spine, the method comprising the steps of:

imaging a patient anatomy including a surgical site;

selecting a minimally invasive pathway including a pedicle of a first cervical vertebra, and a lateral mass of a second cervical vertebra of the patient anatomy;

creating a cavity in the pedicle with at least one surgical instrument including a surgical navigation component generating a signal representative of a position of the surgical instrument relative to the surgical site; and engaging a bone screw with the at least a portion of the pedicle with a surgical driver including a surgical navigation component generating a signal representative of a position of the surgical driver and/or bone screw relative to the surgical site, the bone screw including a receiver including a first arm connected to a first extension and a second arm connected to a second extension, the arms being connected to the extensions via a break away surface, the arms including a proximal shoulder disposed about the break away surface and the receiver further including an implant receiving surface, the proximal shoulder and the implant receiving surface defining an implant cavity, and a threaded shaft connectable with the receiver and engageable with the at least a portion of the pedicle.

18. A method as recited in claim 17, wherein the receiver defines a longitudinal axis and a proximal most end surface defines a transverse plane, the break away surface being axially spaced from the transverse plane.

19. A method as recited in claim 17, wherein the step of creating a cavity includes disposing a guide member with the patient anatomy, the guide member being configured for disposal of the at least one surgical instrument and an image guide being oriented relative to a sensor to communicate a signal representative of a position of the guide member, the guide member including an end effector of a robotic arm.

* * * * *